(12) United States Patent
Bolton et al.

(10) Patent No.: US 7,880,010 B2
(45) Date of Patent: *Feb. 1, 2011

(54) CRYSTALLINE FORMS OF A DIMETHYLPHENYL COMPOUND

(75) Inventors: Jennifer Bolton, Edinburgh (GB);
Robert S. Chao, Santa Clara, CA (US);
Miroslav Rapta, Sunnyvale, CA (US);
Lisa Williams, Santa Clara, CA (US);
Richard D. Wilson, El Sobrante, CA (US)

(73) Assignee: Theravance, Inc., South San Francisco, CA (US)

( * ) Notice: Subject to any disclaimer, the term of this patent is extended or adjusted under 35 U.S.C. 154(b) by 861 days.

This patent is subject to a terminal disclaimer.

(21) Appl. No.: 11/789,154

(22) Filed: Apr. 24, 2007

(65) Prior Publication Data

US 2007/0249674 A1    Oct. 25, 2007

Related U.S. Application Data

(60) Provisional application No. 60/794,709, filed on Apr. 25, 2006.

(51) Int. Cl.
*C07D 211/46* (2006.01)
*A61K 31/445* (2006.01)

(52) U.S. Cl. ..................... 546/222; 514/327
(58) Field of Classification Search ............... 546/222; 514/327
See application file for complete search history.

(56) References Cited

U.S. PATENT DOCUMENTS

| 6,268,533 B1 | 7/2001 | Gao et al. |
| 6,576,793 B1 | 6/2003 | Moran et al. |
| 6,653,323 B2 | 11/2003 | Moran et al. |
| 6,670,376 B1 | 12/2003 | Moran et al. |
| 6,693,202 B1 | 2/2004 | Aggen et al. |
| 7,141,671 B2 | 11/2006 | Mammen et al. |
| 7,345,175 B2 * | 3/2008 | Mammen et al. ............ 546/242 |
| 7,524,965 B2 * | 4/2009 | Colson et al. ............... 546/216 |
| 2003/0018019 A1 | 1/2003 | Meade et al. |
| 2004/0167167 A1 | 8/2004 | Mammen et al. |
| 2004/0209860 A1 | 10/2004 | Mammen et al. |
| 2004/0209915 A1 | 10/2004 | Mammen et al. |
| 2006/0035933 A1 | 2/2006 | Mammen et al. |
| 2006/0116398 A1 | 6/2006 | Mammen et al. |
| 2006/0223858 A1 | 10/2006 | Mammen et al. |
| 2006/0223859 A1 | 10/2006 | Mammen et al. |
| 2006/0223860 A1 | 10/2006 | Mammen et al. |
| 2006/0229334 A1 | 10/2006 | Mammen et al. |
| 2007/0037984 A1 | 2/2007 | Mammen et al. |
| 2007/0088054 A1 | 4/2007 | Mammen et al. |

FOREIGN PATENT DOCUMENTS

| EP | 0 747 355 A1 | 12/1996 |
| WO | WO 95/06635 A1 | 3/1995 |
| WO | WO 2004/074246 | 9/2004 |

OTHER PUBLICATIONS

Chaumeil, J.C., Methods and Findings in Experimental and Clinical Pharmacology, Apr. 1998, vol. 20, No. 3, pp. 211-215.*
Isogaya et al., "Binding Pockets of the $\beta_1$- and $\beta_2$-Adrenergic Receptors for Subtype-Selective Agonists", Molecular Pharmacology, 56: pp. 875-885 (1999).
Naito et al., "Selective Muscarinic Antagonist. II. [1)] Synthesis and Antimuscarinic Properties of Biphenylylcarbamate Derivatives", Chem. Pharm. Bull., vol. 46, No. 8, pp. 1286-1294 (1998).
"New long acting $\beta_2$ agonists", Expert Opin. Ther. Patents, 13(2), pp. 273-277 (2003).

* cited by examiner

*Primary Examiner*—Rita J Desai
*Assistant Examiner*—David K O'Dell
(74) *Attorney, Agent, or Firm*—Jeffrey A. Hagenah

(57) ABSTRACT

The invention relates to crystalline free base forms of biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester or a solvate thereof. This invention also relates to pharmaceutical compositions containing or prepared from such crystalline forms; processes and intermediates useful for preparing such crystalline forms; and methods of using such crystalline forms to, for example, treat a pulmonary disorder.

13 Claims, 6 Drawing Sheets

CRYSTALLINE FORMS OF A DIMETHYLPHENYL COMPOUND

CROSS-REFERENCE TO RELATED APPLICATIONS

This application claims the benefit of U.S. Provisional Application No. 60/794,709, filed on Apr. 25, 2006; the entire disclosure of which is incorporated herein by reference in its entirety.

BACKGROUND OF THE INVENTION

1. Field of the Invention

The present invention relates to novel crystalline free base forms of a dimethylphenyl compound, which compound is expected to be useful as a therapeutic agent for treating pulmonary disorders. This invention also relates to pharmaceutical compositions containing or prepared from such crystalline forms; processes and intermediates useful for preparing such crystalline forms; and methods of using such crystalline forms to, for example, treat a pulmonary disorder.

2. State of the Art

Commonly-assigned U.S. application Ser. No. 11/789,300, filed on even date herewith now U.S. Pat. No. 7,524,965 B2) and U.S. Provisional Application No. 60/794,702, filed Apr. 25, 2006, (the disclosures of which are incorporated herein by reference in their entirety) disclose novel dialkylphenyl compounds that are useful as therapeutic agents for treating pulmonary disorders, such as chronic obstructive pulmonary disease (COPD) and asthma. In particular, the compound, biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]-piperidin-4-yl ester is specifically disclosed in this application as possessing both muscarinic antagonist and $\beta_2$ adrenergic receptor agonist activity. The chemical structure of biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester is represented by formula I:

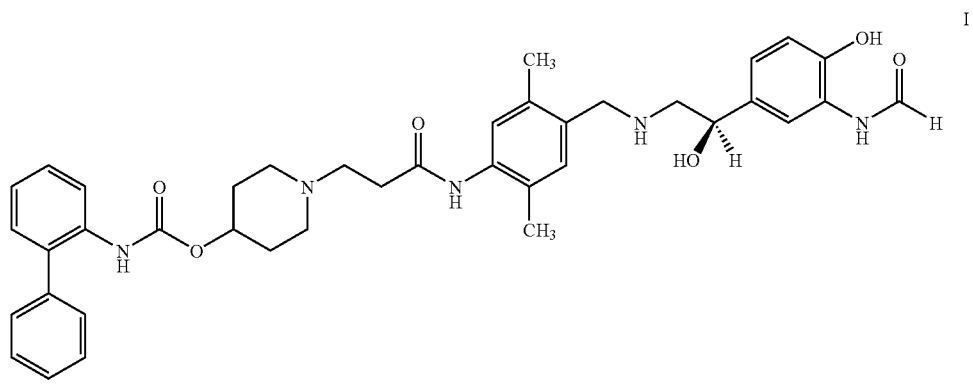

Therapeutic agents useful for treating pulmonary disorders are advantageously administered directly into the respiratory tract by inhalation. In this regard, several types of pharmaceutical inhalation devices have been developed for administering therapeutic agents by inhalation including dry powder inhalers (DPI), metered-dose inhalers (MDI) and nebulizer inhalers. When preparing pharmaceutical compositions and formulations for use in such devices, it is highly desirable to have a crystalline form of the therapeutic agent that is neither hygroscopic nor deliquescent and which has a relatively high melting point (i.e. greater than about 130° C.) thereby allowing the material to be micronized without significant decomposition or loss of crystallinity.

No crystalline forms of the compound of formula I have been disclosed previously. Accordingly, a need exists for a stable, non-deliquescent crystalline form of the compound of formula I that has an acceptable level of hygroscopicity and a relatively high melting point.

SUMMARY OF THE INVENTION

The present invention relates to crystalline free base forms of biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester or a solvate thereof. Surprisingly, such crystalline free base forms of the compound of formula I have been found not to be deliquescent, even when exposed to atmospheric moisture. Additionally, such crystalline forms have an acceptable level of hygroscopicity and a high melting point, e.g., greater than about 130° C.

In a particular aspect, this invention relates to a crystalline free base form of biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester or a solvate thereof in micronized form.

Among other uses, a crystalline free base form of the compound of formula I is useful for preparing pharmaceutical compositions that are expected to be useful for treating pulmonary disorders. Accordingly, in another of its composition aspects, the present invention relates to a pharmaceutical composition comprising a pharmaceutically acceptable carrier and a crystalline free base form of biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester or a solvate thereof.

If desired, the crystalline forms of the present invention can be administered in combination with other therapeutic agents, such as a steroidal anti-inflammatory agent. Accordingly, in another of its composition aspects, this invention relates to a pharmaceutical composition comprising (a) a crystalline free base form of biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester or a solvate thereof; and (b) a second therapeutic agent. In yet another of its composition aspects, this invention relates to a pharmaceutical composition comprising (a) a crystalline free base form of biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)-ethyl]piperidin-4-yl ester or a solvate thereof; (b) a second therapeutic agent; and (c) a pharmaceutically acceptable carrier.

In still another of its composition aspects, this invention relates to a combination of therapeutic agents, the combination comprising (a) a crystalline free base form of biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester or a solvate thereof; and (b) a second therapeutic agent. In another of its composition aspects, this invention relates to a combination of pharmaceutical compositions, the combination comprising (a) a pharmaceutical composition comprising a crystalline free base form of biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester or a solvate thereof and a pharmaceutically acceptable carrier; and (b) a pharmaceutical composition comprising a second therapeutic agent and a pharmaceutically acceptable carrier.

The compound of formula I possesses both $\beta 2$ adrenergic receptor agonist activity and muscarinic receptor antagonist activity. Accordingly, crystalline free base forms of the compound of formula I are expected to be useful as therapeutic agents for treating pulmonary disorders, such as asthma and chronic obstructive pulmonary disease.

Accordingly, in one of its method aspects, this invention relates to a method for treating a pulmonary disorder, the method comprising administering to a patient in need of treatment a therapeutically effective amount of a crystalline free base form of biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester or a solvate thereof.

This invention also relates to a method of treating chronic obstructive pulmonary disease or asthma, the method comprising administering to a patient a therapeutically effective amount of a crystalline free base form of biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester or a solvate thereof.

Additionally, in another of its method aspects, this invention relates to a method of producing bronchodilation in a mammal, the method comprising administering to a mammal a bronchodilation-producing amount of a crystalline free base form of biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester or a solvate thereof.

This invention also relates to a method of antagonizing a muscarinic receptor and agonizing a $\beta 2$ adrenergic receptor in a mammal, the method comprising administering to the mammal a crystalline free base form of biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester or a solvate thereof.

This invention also relates to processes for preparing a free base form of the compound of formula I. Accordingly, in another of its method aspects, this invention relates to a process for preparing a crystalline free base form of biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)-ethyl]piperidin-4-yl ester, the process comprising:

(a) providing a solution of biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester in a diluent;

(b) adding a counter solvent to the solution from step (a) to produce a cloud point.

Optionally, this process further includes the step of:

(c) adding a seed crystal of a crystalline free base form of biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester to the product of step (b). In a particular embodiment of these processes, the diluent is methanol and the counter solvent is water.

Additionally, this invention relates to a crystalline free base form of biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester or a solvate thereof for use in therapy. This invention also relates to use of such a crystalline free base form for the manufacture of a medicament for the treatment of a pulmonary disorder. Other aspects and embodiments of this invention are disclosed herein.

BRIEF DESCRIPTION OF THE DRAWINGS

Various aspects of the present invention are illustrated by reference to the accompanying drawings.

DETAILED DESCRIPTION OF THE INVENTION

Figure 1:
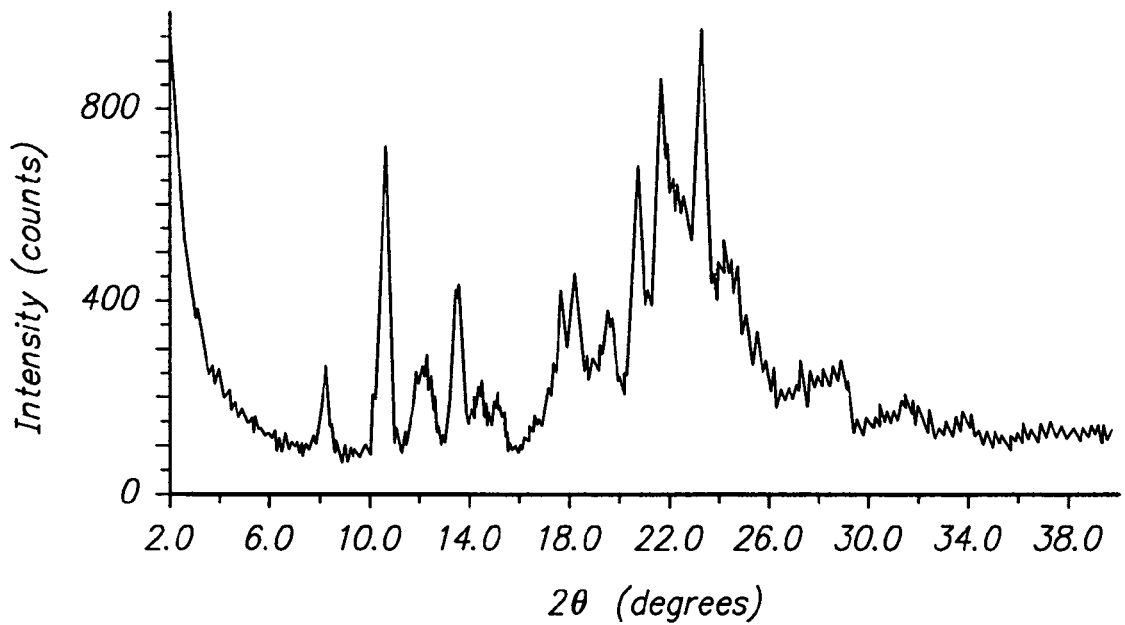
FIGS. 1, 2 and 3 show powder x-ray diffraction (PXRD) patterns for Forms I, II and III, respectively, of the crystalline free base of biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester.

This invention relates to crystalline free base forms of biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester or a solvate thereof. The active therapeutic agent in these salts (i.e., the compound of formula I) contains one chiral center having the (R) configuration. However, it will be understood by those skilled in the art that minor amounts of the (S) stereoisomer may be present in the compositions of this invention unless otherwise indicated, provided that any utility of the composition as a whole is not eliminated by the presence of such an isomer.

The compound of formula I has been named using the commercially-available AutoNom software (MDL, San Leandro, Calif.).

Definitions

When describing the compounds, compositions, methods and processes of this invention, the following terms have the following meanings unless otherwise indicated.

The term "melting point" as used herein means the temperature at which the maximum endothermic heat flow is observed by differential scanning calorimetry.

The term "mass median diameter" or "MMD" when used to refer to particles means the diameter such that half the mass of the particles is contained in particles with larger diameter and half is contained in particles with smaller diameter.

The term "micronized" or "in micronized form" means particles in which at least about 90 percent of the particles have a diameter of less than about 10 µm unless otherwise indicated.

The term "solvate" means a complex or aggregate formed by one or more molecules of a solute, i.e. a free base form of the compound of formula I, and one or more molecules of a solvent. Such solvates typically have a substantially fixed molar ratio of solute and solvent. This term also includes clathrates, including clathrates with water. Representative solvents include, by way of example, water, methanol, ethanol, isopropanol, acetic acid and the like. When the solvent is water, the solvate formed is a hydrate.

The term "therapeutically effective amount" means an amount sufficient to effect treatment when administered to a patient in need of treatment.

The term "treating" or "treatment" as used herein means the treating or treatment of a disease or medical condition (such as COPD) in a patient, such as a mammal (particularly a human) that includes:

(a) preventing the disease or medical condition from occurring, i.e., prophylactic treatment of a patient;
(b) ameliorating the disease or medical condition, i.e., eliminating or causing regression of the disease or medical condition in a patient;
(c) suppressing the disease or medical condition, i.e., slowing or arresting the development of the disease or medical condition in a patient; or
(d) alleviating the symptoms of the disease or medical condition in a patient.

The term "unit dosage form" refers to a physically discrete unit suitable for dosing a patient, i.e., each unit containing a predetermined quantity of a salt of the invention calculated to produce the desired therapeutic effect either alone or in combination with one or more additional units. For example, such unit dosage forms may be dry powder inhaler capsules, a metered dose from a metered dose inhaler, capsules, tablets, pills, and the like.

All other terms used herein are intended to have their ordinary meaning as understood by those of ordinary skill in the art to which they pertain.

Representative Crystalline Free Base Forms of the Invention

Biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester has been discovered to exist in at least three different crystalline free base forms. For purposes of this invention, these forms are identified herein as Form I, Form II and Form III. These crystalline forms of the compound of formula I can be distinguished by at least the following properties:

Form I: A differential scanning calorimetry (DSC) trace that exhibit a peak in endothermic heat flow at about 132° C. to about 138° C.; and a powder x-ray diffraction (PXRD) pattern having significant diffraction peaks, among other peaks, at 2θ values of about 17.7±0.3, 18.2±0.3, 21.7±0.3 and 23.2±0.3.

Form II: A differential scanning calorimetry (DSC) trace that exhibit a peak in endothermic heat flow at about 142° C. to about 150° C.; and a powder x-ray diffraction (PXRD) pattern having significant diffraction peaks, among other peaks, at 2θ values of about 20.7±0.3, 21.6±0.3, 22.5±0.3 and 23.2±0.3.

Form III: A differential scanning calorimetry (DSC) trace that exhibit a peak in endothermic heat flow at about 134° C. to about 140° C.; and a powder x-ray diffraction (PXRD) pattern having significant diffraction peaks, among other peaks, at 2θ values of about 15.5±0.3, 18.1±0.3, 19.2±0.3 and 21.8±0.3.

The crystalline free base forms of biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester are prepared by crystallization of biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester or a solvate thereof.

In one method of preparation, the crystalline free base forms of the compound of formula I are prepared by forming a slurry of the compound in a solvent and stirring the resulting slurry for a sufficient period of time to form crystalline material. Typically, such slurries are stirred for about 24 to about 72 hours at ambient temperature (i.e., about 20° C. to about 30° C.). Generally, the slurry will comprise about 35 mg to about 45 mg, i.e., about 40 mg, of compound per milliliter of solvent. In some cases, the choice of solvent will determine which crystalline free base form is produced from the slurry. For example, when the solvent is acetonitrile, Form I has been produced as the predominate form. Alternatively, when the solvent is isopropanol, Form II has been produced as the predominate form. Additionally, when the solvent is ethanol, Form III has been produced as the predominate form. In addition to solvent, other factors may affect which solid form is produced.

In another method of preparation, biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]-piperidin-4-yl ester is dissolved in a diluent, such as methanol, ethanol, isopropanol, ethyl acetate, acetonitrile and the like, and a counter solvent (anti-solvent), such as water and the like, is added resulting in the formation of crystalline free base. Generally, the crystallization procedure can be conducted at ambient temperature or by heating the mixture and then allowing it to cool to ambient temperature. In a particular embodiment of this method, the diluent is methanol and the counter solvent is water.

The biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)-ethyl]piperidin-4-yl ester employed in this invention can be readily prepared from commercially-available starting materials and reagents using the procedures described in the Examples below; or by using the procedures described in the commonly-assigned U.S. application described in the Background section of this application.

A process of preparing a crystalline free base form of this invention can optionally include the use of a seed crystal to produce predominately a particular free base form. For example, by using a seed crystal of Form II, a crystalline free base form of a compound of formula I can be prepared having essentially the same form as the seed crystal, i.e. Form II. Such seed crystals can be used when initially forming the crystalline free base form or they can be used to recrystallize a crystalline or partially crystalline free base form.

Typically, seed crystals are prepared by slow crystallization without stirring and without applying cooling. By way of illustration, to obtain seed crystals, the compound of formula I is typically dissolved in a diluent at a temperature sufficient to provide dissolution. For example, the compound of formula I is dissolved in a 1:2 mixture of acetonitrile and water at about 75° C. to about 80° C. and then allowed to cool to ambient temperature for about 12 hours to 24 hours to provide a crystalline free base form. In another embodiment, methanol containing about 40% to about 80% water by volume is used as the diluent. The resulting crystals are isolated by filtration or other conventional means. Alternatively, seed crystals may be obtain from a previous preparation of crystalline material.

In a particular embodiment of the recrystallization process using seed crystals, a free base form of the compound of formula I is dissolved in methanol (typically about 120 mL to about 160 mL, including 140 mL, of methanol per gram of compound) at ambient temperature and water is added until a cloud point is reached. Seed crystals are then added (typically about 1 to about 5 mg of seed crystal per gram of compound). The resulting mixture is stirred at ambient temperature during which time the compound of formula I crystallizes. The resulting crystals are isolated using conventional procedures, such as filtration. It will be appreciated that the specific temperatures used for the crystallization or recrystallization process will be selected depending on the character of the diluent and the concentration of the crystalline salt in the diluent. Additionally, the recrystallization process can be conducted using either evaporation or a counter solvent to facilitate crystallization instead of cooling.

In one aspect of this invention, the crystalline free base forms of this invention are defined by their physical and/or spectral characteristics. Accordingly, in one embodiment, this invention relates to a crystalline free base form of the compound of formula I characterized by a powder x-ray diffraction (PXRD) pattern having significant diffraction peaks at 2θ values of about 17.7±0.3, 18.2±0.3, 21.7±0.3 and 23.2±0.3. In a particular aspect of this embodiment, this invention relates to a crystalline free base form characterized by a powder x-ray diffraction pattern in which the peak positions are substantially in accordance with those shown in FIG. 1.

In another embodiment, this invention relates to a crystalline free base form of the compound of formula I characterized by a powder x-ray diffraction (PXRD) pattern having significant diffraction peaks at 2θ values of about 20.7±0.3, 21.6±0.3, 22.5±0.3 and 23.2±0.3. In a particular aspect of this embodiment, this invention relates to a crystalline free base form characterized by a powder x-ray diffraction pattern in which the peak positions are substantially in accordance with those shown in FIG. 2.

In still another embodiment, this invention relates to a crystalline free base form of the compound of formula I characterized by a powder x-ray diffraction (PXRD) pattern having significant diffraction peaks at 2θ values of about 15.5±0.3, 18.1±0.3, 19.2±0.3 and 21.8±0.3. In a particular aspect of this embodiment, this invention relates to a crystalline free base form characterized by a powder x-ray diffraction pattern in which the peak positions are substantially in accordance with those shown in FIG. 3.

Figure 4:
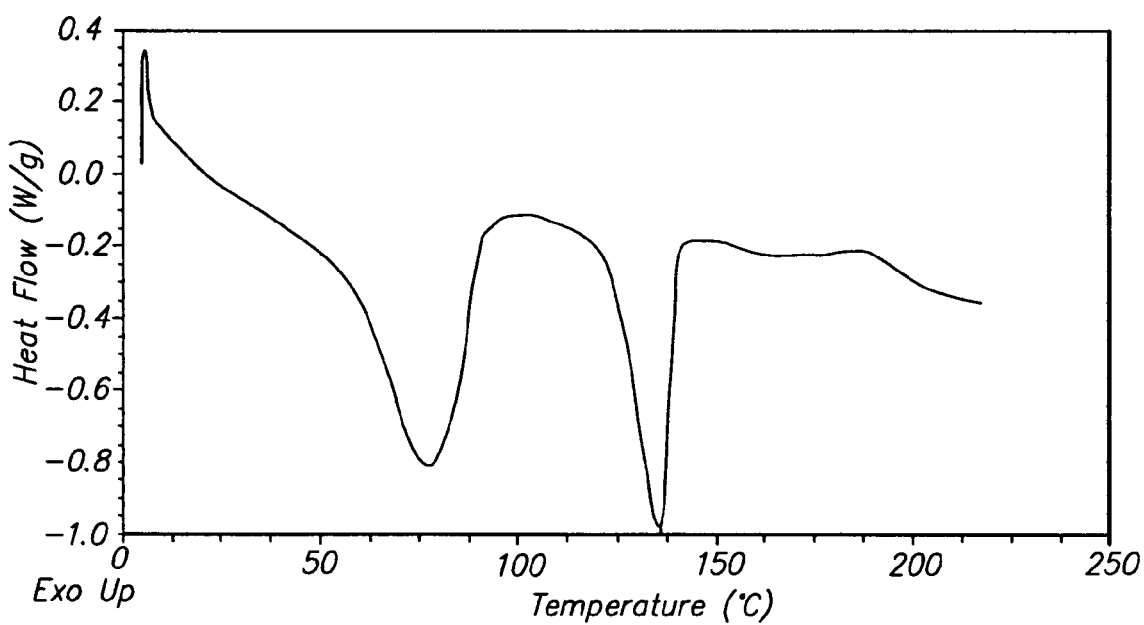
FIGS. 4, 5 and 6 show differential scanning calorimetry (DSC) traces for Forms I, II and III, respectively, of the crystalline free base of biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester.

In yet another embodiment, this invention relates to a crystalline free base form of the compound of formula I having a DSC trace substantially in accordance with the trace shown in FIG. 4. In other embodiment, this relates to a crystalline free base form of the compound of formula I having a DSC trace substantially in accordance with the trace shown in FIG. 5. In yet another embodiment, this relates to a crystalline free base form of the compound of formula I having a DSC trace substantially in accordance with the trace shown in FIG. 6.

A crystalline free base of Form II has been demonstrated to have a reversible sorption/desorption profile with less than about 0.5% weight gain in the humidity range of 40% relative humidity to 75% relative humidity.

These properties of the crystalline free base forms of this invention are further illustrated in the Examples below.

Pharmaceutical Compositions, Combinations and Formulations

The crystalline free base forms of this invention are typically administered to a patient in the form of a pharmaceutical composition or formulation. Such pharmaceutical compositions may be administered to the patient by any acceptable route of administration including, but not limited to, inhaled, oral, nasal, topical (including transdermal) and parenteral modes of administration.

Accordingly, in one of its compositions aspects, this invention relates to a pharmaceutical composition comprising a pharmaceutically acceptable carrier or excipient and a crystalline free base form of the compound of formula I. Optionally, such pharmaceutical compositions may contain other therapeutic and/or formulating agents if desired.

The pharmaceutical compositions of this invention typically contain a therapeutically effective amount of a crystalline free base form of the compound of formula I. Those skilled in the art will recognize, however, that a pharmaceutical composition may contain more than a therapeutically effective amount, i.e., bulk compositions, or less than a therapeutically effective amount, i.e., individual unit doses designed for multiple administration to achieve a therapeutically effective amount.

Typically, the pharmaceutical composition will contain from about 0.01 to about 95 percent by weight of the therapeutic agent; including, from about 0.01 to about 30 percent by weight; such as from about 0.01 to about 10 percent by weight of the therapeutic agent.

Any conventional carrier or excipient may be used in the pharmaceutical compositions of this invention. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those of ordinary skill in the pharmaceutical arts.

The carriers or excipients used in the pharmaceutical compositions of this invention are commercially available. For example, such materials can be purchased from Sigma (St. Louis, Mo.). By way of further illustration, conventional formulation techniques are well known to those of ordinary skill in the art as exemplified by the teachings in *Remington: The Science and Practice of Pharmacy*, 20th Edition, Lippincott Williams & White, Baltimore, Md. (2000); and H. C. Ansel et al., *Pharmaceutical Dosage Forms and Drug Delivery Systems*, 7th Edition, Lippincott Williams & White, Baltimore, Md. (1999).

Representative examples of materials which can serve as pharmaceutically acceptable carriers include, but are not limited to, the following: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) compressed propellant gases, such as chlorofluorocarbons and hydrofluorocarbons; and (22) other non-toxic compatible substances employed in pharmaceutical compositions.

The pharmaceutical compositions of this invention are typically prepared by thoroughly and intimately mixing or blending a crystalline free base form of the invention with a pharmaceutically acceptable carrier and any optional ingredients. If necessary or desired, the resulting uniformly blended mixture can then be shaped or loaded into tablets, capsules, pills, canisters, cartridges, dispensers and the like using conventional procedures and equipment.

In one embodiment, the pharmaceutical compositions of this invention are suitable for inhaled administration. Suitable pharmaceutical compositions for inhaled administration will typically be in the form of an aerosol or a powder. Such compositions are generally administered using well-known delivery devices, such as a nebulizer inhaler, a metered-dose inhaler (MDI), a dry powder inhaler (DPI) or a similar delivery device.

In a specific embodiment of this invention, the pharmaceutical composition comprising the therapeutic agent is administered by inhalation using a nebulizer inhaler. Such nebulizer devices typically produce a stream of high velocity air that causes the pharmaceutical composition comprising the therapeutic agent to spray as a mist that is carried into the patient's respiratory tract. Accordingly, when formulated for use in a nebulizer inhaler, the therapeutic agent is typically dissolved in a suitable carrier to form a solution. Alternatively, the therapeutic agent can be micronized and combined with a suitable carrier to form a suspension of micronized particles. Nebulizer devices suitable for administering therapeutic agents by inhalation are well known to those of ordinary skill in the art or such devices are commercially available. For example, representative nebulizer devices or products include the Respimat Softmist Inhaler (Boehringer Ingelheim); the AERx Pulmonary Delivery System (Aradigm Corp.); the PARI LC Plus Reusable Nebulizer (Pari GmbH); and the like.

A representative pharmaceutical composition for use in a nebulizer inhaler comprises an isotonic aqueous solution comprising from about 0.05 µg/mL to about 10 mg/mL of a compound of formula I. Such compositions are typically prepared by dissolving a crystalline free base form of the compound of formula I in isotonic saline. In one embodiment, such a solution has a pH of about 4 to about 6.

In another specific embodiment of this invention, the pharmaceutical composition comprising the therapeutic agent is administered by inhalation using a dry powder inhaler. Such dry powder inhalers typically administer the therapeutic agent as a free-flowing powder that is dispersed in a patient's air-stream during inspiration. In order to achieve a free-flowing powder, the therapeutic agent is typically formulated with a suitable excipient such as lactose, starch, mannitol, dextrose, polylactic acid (PLA), polylactide-co-glycolide (PLGA) or combinations thereof. Typically, the therapeutic agent is micronized and combined with a suitable carrier to form a blend suitable for inhalation.

A representative pharmaceutical composition for use in a dry powder inhaler comprises dry milled lactose and micronized particles of a crystalline free base form of the compound of formula I.

Such a dry powder formulation can be made, for example, by combining the lactose with the therapeutic agent and then dry blending the components. Alternatively, if desired, the therapeutic agent can be formulated without an excipient. The pharmaceutical composition is then typically loaded into a dry powder dispenser, or into inhalation cartridges or capsules for use with a dry powder delivery device.

Dry powder inhaler delivery devices suitable for administering therapeutic agents by inhalation are well known to those of ordinary skill in the art or such devices are commercially available. For example, representative dry powder inhaler delivery devices or products include Aeolizer (Novartis); Airmax (IVAX); ClickHaler (Innovata Biomed); Diskhaler (GlaxoSmithKline); Diskus/Accuhaler (GlaxoSmithKline); Easyhaler (Orion Pharma); Eclipse (Aventis); FlowCaps (Hovione); Handihaler (Boehringer Ingelheim); Pulvinal (Chiesi); Rotahaler (GlaxoSmithKline); SkyeHaler/Certihaler (SkyePharma); Twisthaler (Schering-Plough); Turbuhaler (AstraZeneca); Ultrahaler (Aventis); and the like.

In yet another specific embodiment of this invention, the pharmaceutical composition comprising the therapeutic agent is administered by inhalation using a metered-dose inhaler. Such metered-dose inhalers typically discharge a measured amount of the therapeutic agent using a compressed propellant gas. Accordingly, pharmaceutical compositions administered using a metered-dose inhaler typically comprise a solution or suspension of the therapeutic agent in a liquefied propellant. Any suitable liquefied propellant may be employed including chlorofluorocarbons, such as $CCl_3F$, and hydrofluoroalkanes (HFAs), such as 1,1,1,2-tetrafluoroethane (HFA 134a) and 1,1,1,2,3,3,3-heptafluoro-n-propane, (HFA 227). Due to concerns about chlorofluorocarbons affecting the ozone layer, formulations containing HFAs are generally preferred. Additional optional components of HFA formulations include co-solvents, such as ethanol or pentane, and surfactants, such as sorbitan trioleate, oleic acid, lecithin, and glycerin.

A representative pharmaceutical composition for use in a metered-dose inhaler comprises from about 0.01% to about 5% by weight of a crystalline free base form of the compound of formula I; from about 0% to about 20% by weight ethanol; and from about 0% to about 5% by weight surfactant; with the remainder being an HFA propellant.

Such compositions are typically prepared by adding chilled or pressurized hydrofluoroalkane to a suitable container containing the therapeutic agent, ethanol (if present) and the surfactant (if present). To prepare a suspension, the therapeutic agent is micronized and then combined with the propellant. The formulation is then loaded into an aerosol canister, which forms a portion of a metered-dose inhaler device.

Metered-dose inhaler devices suitable for administering therapeutic agents by inhalation are well known to those of ordinary skill in the art or such devices are commercially available. For example, representative metered-dose inhaler devices or products include AeroBid Inhaler System (Forest Pharmaceuticals); Atrovent Inhalation Aerosol (Boehringer Ingelheim); Flovent (GlaxoSmithKline); Maxair Inhaler (3M); Proventil Inhaler (Schering); Serevent Inhalation Aerosol (GlaxoSmithKline); and the like.

In another embodiment, the pharmaceutical compositions of this invention are suitable for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a crystalline free base form of the present invention as an active ingredient.

When intended for oral administration in a solid dosage form (i.e., as capsules, tablets, pills and the like), the pharmaceutical compositions of this invention will typically comprise a crystalline free base form of the present invention as the active ingredient and one or more pharmaceutically acceptable carriers, such as sodium citrate or dicalcium phosphate. Optionally or alternatively, such solid dosage forms may also comprise: (1) fillers or extenders, such as starches, lactose, sucrose, glucose, mannitol, and/or silicic acid; (2) binders, such as carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and/or sodium carbonate; (5) solution retarding agents, such as paraffin; (6) absorption accelerators, such as quaternary ammonium compounds; (7) wetting agents, such as cetyl alcohol and/or glycerol monostearate; (8) absorbents, such as kaolin and/or bentonite clay; (9) lubricants, such as talc, calcium stearate, magnesium stearate, solid polyethylene glycols, sodium lauryl sulfate, and/or mixtures thereof; (10) coloring agents; and (11) buffering agents.

Release agents, wetting agents, coating agents, sweetening, flavoring and perfuming agents, preservatives and antioxidants can also be present in the pharmaceutical compositions of this invention. Examples of pharmaceutically acceptable antioxidants include: (1) water-soluble antioxidants, such as ascorbic acid, cysteine hydrochloride, sodium bisulfate, sodium metabisulfate, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like. Coating agents for tablets, capsules, pills and like, include those used for enteric coatings, such as cellulose acetate phthalate (CAP), polyvinyl acetate phthalate (PVAP), hydroxypropyl methylcellulose phthalate, methacrylic acid/methacrylic acid ester copolymers, cellulose acetate trimellitate (CAT), carboxymethyl ethyl cellulose (CMEC), hydroxypropyl methyl cellulose acetate succinate (HPMCAS), and the like.

If desired, the pharmaceutical compositions of the present invention may also be formulated to provide slow or controlled release of the active ingredient using, by way of example, hydroxypropyl methyl cellulose in varying proportions; or other polymer matrices, liposomes and/or microspheres.

In addition, the pharmaceutical compositions of the present invention may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Suitable liquid dosage forms for oral administration include, by way of illustration, pharmaceutically acceptable emulsions, microemulsions, solutions, suspensions, syrups and elixirs. Such liquid dosage forms typically comprise the active ingredient and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (esp., cottonseed, groundnut, corn, germ, olive, castor and sesame oils), glycerol, tetrahydrofuryl alcohol, polyethylene glycols and fatty acid esters of sorbitan, and mixtures thereof. Suspensions, in addition to the active ingredient, may contain suspending agents such as, for example, ethoxylated isostearyl alcohols, polyoxyethylene sorbitol and sorbitan esters, microcrystalline cellulose, aluminium metahydroxide, bentonite, agar-agar and tragacanth, and mixtures thereof. Of course, when administered as a solution in liquid dose form, the crystalline free base form is no longer in crystalline form but is dissolved in the liquid carrier.

When intended for oral administration, the pharmaceutical compositions of this invention may be packaged in a unit dosage form. The term "unit dosage form" means a physically discrete unit suitable for dosing a patient, i.e., each unit containing a predetermined quantity of active agent calculated to produce the desired therapeutic effect either alone or in combination with one or more additional units. For example, such unit dosage forms may be capsules, tablets, pills, and the like.

The crystalline free base forms of this invention can also be administered transdermally using known transdermal delivery systems and excipients. For example, a crystalline free base form can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

Additionally, the crystalline free base forms of this invention can be administered parenterally, i.e., intravenously, subcutaneously or intramuscularly. For parenteral administration, a crystalline free base form of the compound of formula I is typically dissolved in a carrier acceptable for parenteral administration, such as sterile water, saline, vegetable oil and the like. By way of illustration, an intravenous composition typically comprises a sterile aqueous solution prepared from a crystalline free base form of a compound of formula I, wherein the solution has a pH in the range of about 4 to about 7.

If desired, the crystalline free base forms of this invention may be administered in combination with one or more other therapeutic agents. In this embodiment, a crystalline free base form of this invention is either physically mixed with the other therapeutic agent to form a composition containing both agents; or each agent is present in separate and distinct compositions which are administered to the patient simultaneously or sequentially.

For example, a crystalline free base form of the compound of formula I can be combined with second therapeutic agent using conventional procedures and equipment to form a composition comprising a crystalline free base form of the compound of formula I and a second therapeutic agent. Additionally, the therapeutic agents may be combined with a pharmaceutically acceptable carrier to form a pharmaceutical composition comprising a crystalline free base form of the compound of formula I, a second therapeutic agent and a pharmaceutically acceptable carrier. In this embodiment, the components of the composition are typically mixed or blended to create a physical mixture. The physical mixture is then administered in a therapeutically effective amount using any of the routes described herein.

Alternatively, the therapeutic agents may remain separate and distinct before administration to the patient. In this embodiment, the therapeutic agents are not physically mixed together before administration but are administered simultaneously or sequentially as separate compositions. For example, a crystalline free base form of the compound of formula I can be administered by inhalation simultaneously or sequentially with another therapeutic agent using an inhalation delivery device that employs separate compartments (e.g. blister packs) for each therapeutic agent. Alternatively, the combination may be administered using separate delivery devices, i.e., one delivery device for each therapeutic agent. Additionally, the therapeutic agents can be delivered by different routes of administration, i.e., one by inhalation and the other by oral administration.

Any therapeutic agent compatible with the crystalline free base forms of the present invention may be used in combination with such forms. In a particular embodiment, the second therapeutic agent is one that is effectively administered by inhalation. By way of illustration, representative types of therapeutic agents that may be used with the compounds of this invention include, but are not limited to, anti-inflammatory agents, such as steroidal anti-inflammatory agents (including corticosteroids and glucocorticoids), non-steroidal anti-inflammatory agents (NSAIDs), and $PDE_4$ inhibitors; bronchodilators, such as $PDE_3$ inhibitors, adenosine 2b modulators and $β_2$ adrenergic receptor agonists; antiinfective agents, such as Gram-positive antibiotics, Gram-negative antibiotics, and antiviral agents; antihistamines; protease inhibitors; afferent blockers, such as $D_2$ agonists and neurokinin modulators; and muscarinic receptor antagonists (antichlolinergic agents). Numerous examples of such therapeutic agents are well known in the art. Suitable doses for the other therapeutic agents administered in combination with a compound of the invention are typically in the range of about 0.05 µg/day to about 500 mg/day.

In a particular embodiment of this invention, a crystalline free base form of the compound of formula I is administered in combination with a steroidal anti-inflammatory agent. Representative examples of steroidal anti-inflammatory agents that can be used in combination with the crystalline free base forms of this invention include, but are not limited to, beclomethasone dipropionate; budesonide; butixocort propionate; 20R-16α,17α-[butylidenebis(oxy)]-6α,9α-difluoro-11β-hydroxy-17β-(methylthio)androsta-4-en-3-one (RPR-106541); ciclesonide; dexamethasone; 6α,9α-difluoro-17α-[(2-furanylcarbonyl)oxy]-11β-hydroxy-16α-methyl-3-oxoandrosta-1,4-diene-17β-carbothioic acid S-fluoromethyl ester; 6α,9α-difluoro-11β-hydroxy-16α-methyl-17α-[(4-methytl-1,3-thiazole-5-carbonyl)oxy]-3-oxoandrosta-1,4-diene-17β-carbothioic acid S-fluoromethyl ester; 6α,9α-difluoro-11β-hydroxy-16α-methyl-3-oxo-17α-propionyloxyandrosta-1,4-diene-17β-carbothioic acid (S)-(2-oxotetrahydrofuran-3S-yl) ester; flunisolide; fluticasone propionate; methyl prednisolone; mometasone furoate; prednisolone; prednisone; rofleponide; ST-126; triamcinolone acetonide; and the like, or pharmaceutically acceptable salts thereof. Such steroidal anti-inflammatory agents are commercially available or can be prepared using conventional procedures and reagents. For example, the preparation and use of steroidal anti-inflammatory agents is described in U.S. Pat. No. 6,750,210 B2, issued Jun. 15, 2004; U.S. Pat. No. 6,759,398 B2, issued Jul. 6, 2004; U.S. Pat. No. 6,537,983, issued Mar. 25, 2003; U.S. Patent Application Publication No. US 2002/0019378 A1, published Feb. 14, 2002; and references cited therein.

When employed, the steroidal anti-inflammatory agent is typically administered in an amount that has a therapeutically beneficial effect when co-administered with a crystalline free base form of the invention. Typically, the steroidal anti-inflammatory agent will be administered in an amount sufficient to provide from about 0.05 µg to about 500 µg per dose.

The following examples illustrate representative pharmaceutical compositions of the present invention:

Example A

Dry Powder Composition

A micronized crystalline free base form of the compound of formula I (100 mg) is blended with milled lactose (25 g) (e.g., lactose in which not greater than about 85% of the particles have a MMD of about 60 µm to about 90 µm and not less than 15% of the particles have a MMD of less then 15 µm). This blended mixture is then loaded into individual blisters of a peelable blister pack in an amount sufficient to provide about 10 µg to about 500 µg of the compound of formula I per dose. The contents of the blisters are administered using a dry powder inhaler.

Example B

Dry Powder Composition

A micronized crystalline free base form of the compound of formula I (1 g) is blended with milled lactose (200 g) to form a bulk composition having a weight ratio of crystalline free base form to milled lactose of 1:200. The blended composition is packed into a dry powder inhalation device capable of delivering between about 10 µg to about 500 µg of the compound of formula I per dose.

Example C

Dry Powder Composition

A micronized crystalline free base form of the compound of formula I (100 mg) and a micronized steroidal anti-inflammatory agent (500 mg) are blended with milled lactose (30 g). This blended mixture is then loaded into individual blisters of a peelable blister pack in an amount sufficient to provide about 10 µg to about 500 µg of the compound of formula I per dose. The contents of the blisters are administered using a dry powder inhaler.

Example D

Metered-Dose Inhaler Composition

A micronized crystalline free base form of the compound of formula I (10 g) is dispersed in a solution prepared by dissolving lecithin (0.2 g) in demineralized water (200 mL). The resulting suspension is spray dried and then micronized to form a micronized composition comprising particles having a mean diameter less than about 1.5 µg. The micronized composition is then loaded into metered-dose inhaler cartridges containing pressurized 1,1,1,2-tetrafluoroethane in an amount sufficient to provide about 10 μg to about 500 μg of the compound of formula I per dose when administered by the metered dose inhaler.

Example E

Nebulizer Composition

A crystalline free base form of the compound of formula I (25 mg) is dissolved in citrate buffered (pH 5) isotonic saline (125 mL). The mixture is stirred and sonicated until the compound is dissolved. The pH of the solution is checked and adjusted, if necessary, to pH 5 by slowly adding aqueous 1N sodium hydroxide. The solution is administered using a nebulizer device that provides about 10 μg to about 500 μg of the compound of formula I per dose.

Example F

Hard Gelatin Capsules

A crystalline free base form of the compound of formula I (50 g), spray-dried lactose (440 g) and magnesium stearate (10 g) are thoroughly blended. The resulting composition is loaded into a hard gelatin capsule (500 mg of composition per capsule) that are administered orally.

Example G

Oral Suspension

The following ingredients are thoroughly mixed to form a suspension for oral administration:

| Ingredients | Amount |
| --- | --- |
| Crystalline free base form of the compound of formula I | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| VEEGUM ® K (magnesium aluminum silicate) | 1.0 g |
| Flavoring | 0.035 mL |
| Coloring | 0.5 mg |
| Distilled water | q.s. to 100 mL |

The resulting suspension contains 100 mg of active ingredient per 10 mL of suspension. The suspension is administered orally.

Example H

Injectable Composition

A crystalline free base form of the compound of formula I (0.2 g) is blended with 0.4 M sodium acetate buffer solution (2.0 mL). The pH of the resulting solution is adjusted to pH 4 using 0.5 N aqueous hydrochloric acid or 0.5 N aqueous sodium hydroxide, as necessary, and then sufficient water for injection is added to provide a total volume of 20 mL. The mixture is then filtered through a sterile filter (0.22 micron) to provide a sterile solution suitable for administration by injection.

Utility

The compound of formula I possesses both $\beta_2$ adrenergic receptor agonist and muscarinic receptor antagonist activity and therefore, a crystalline free base form of the compound of formula I is expected to be useful as therapeutic agents for treating medical conditions mediated by $\beta_2$ adrenergic receptors or muscarinic receptors, i.e., medical conditions that are ameliorated by treatment with a $\beta_2$ adrenergic receptor agonist or a muscarinic receptor antagonist. Such medical conditions are well known to those of ordinary skill in the art as exemplified by the teachings of Eglen et al., *Muscarinic Receptor Subtypes: Pharmacology and Therapuetic Potential, DN&P* 10(8), 462-469 (1997); Emilien et al., *Current Therapeutic Uses and Potential of beta-Adrenoceptor Agonists and Antagonists, European J. Clinical Pharm.*, 53(6), 389-404 (1998); and references cited therein. Such medical conditions include, by way of example, pulmonary disorders or diseases associated with reversible airway obstruction, such as chronic obstructive pulmonary disease (e.g., chronic and wheezy bronchitis and emphysema), asthma, pulmonary fibrosis and the like. Other conditions include premature labor, depression, congestive heart failure, skin diseases (e.g., inflammatory, allergic, psoriatic and proliferative skin diseases), conditions where lowering peptic acidity is desirable (e.g., peptic and gastric ulceration) and muscle wasting disease.

Accordingly, in one embodiment, this invention relates to a method for treating a pulmonary disorder, the method comprising administering to a patient in need of treatment a therapeutically effective amount of a crystalline free base form of the compound of formula I. When used to treat a pulmonary disorder, the crystalline free base forms of this invention will typically be administered by inhalation in multiple doses per day, in a single dose per day or a single dose per week. Generally, the dose for treating a pulmonary disorder will range from about 10 μg/day to about 500 μg/day.

In one of its method aspects, this invention relates to a method of treating chronic obstructive pulmonary disease or asthma, the method comprising administering to a patient a therapeutically effective amount of a crystalline free base form of the compound of formula I. Generally, the dose for treating COPD or asthma will range from about 10 μg/day to about 500 μg/day. The term "COPD" is understood by those of ordinary skill in the art to include a variety of respiratory conditions, including chronic obstructive bronchitis and emphysema, as exemplified by the teachings of Barnes, *Chronic Obstructive Pulmonary Disease, N. Engl. J. Med.*, 2000: 343:269-78, and references cited therein.

When administered by inhalation, the compounds of this invention typically have the effect of producing bronchodilation. Accordingly, in another of its method aspects, this invention relates to a method of producing bronchodilation in a mammal, the method comprising administering to a mammal a bronchodilation-producing amount of a crystalline free base form of the compound of formula I. Generally, the dose for producing bronchodilation will range from about 10 μg/day to about 500 μg/day.

When used as a therapeutic agent, the crystalline free base forms of this invention are optionally administered in combination with another therapeutic agent or agents. In particular, by administering a crystalline free base form of this invention with a steroidal anti-inflammatory agent, triple therapy, i.e., $\beta_2$ adrenergic receptor agonist activity, muscarinic receptor antagonist activity and anti-inflammatory activity, can be achieved using only two therapeutic agents. Since pharmaceutical compositions (and combinations) containing two therapeutic agents are typically easier to formulate and/or administer compared to compositions containing three therapeutic agents, such two component compositions provide a significant advantage over compositions containing three therapeutic agents. Accordingly, in a particular embodiment, the pharmaceutical compositions, combinations and methods of this invention further comprise a steroidal anti-inflammatory agent.

The properties and utility of crystalline free base forms of the compound of formula I can be demonstrated using various in vitro and in vivo assays well-known to those skilled in the art. For example, representative assays are described in further detail in the following Examples.

EXAMPLES

The following Preparations and Examples are provided to illustrate specific embodiments and aspects of this invention. The illustration of specific embodiments and aspects, however, is not intended to limit the scope of this invention in any way unless specifically indicated.

All reagents, starting materials and solvents used in the following examples were purchased from commercial suppliers (such as Aldrich, Fluka, Sigma and the like) and were used without further purification unless otherwise indicated.

In the following examples, HPLC analysis was typically conducted using an Agilent (Palo Alto, Calif.) Series 1100 instrument with Zorbax Bonus RP 2.1×50 mm columns, supplied by Agilent, (a C14 column), having a 3.5 micron particle size. Detection was by UV absorbance at 214 nm. Mobile phase "A" was 2% acetonitrile, 97.9% water, and 0.1% trifluoroacetic acid (v/v/v); and mobile phase "B" was 89.9% acetonitrile, 10% water, and 0.1% trifluoroacetic acid (v/v/v). HPLC (10-70) data were obtained with a flow rate of 0.5 mL/minute of 10% to 70% mobile phase B gradient over a 6-minute period; HPLC (5-35) data were obtained with a flow rate of 0.5 mL/minute of 5% to 35% mobile phase B gradient over a 5-minute period; and HPLC (10-90) data were obtained with a flow rate of 0.5 mL/minute of 10% to 90% mobile phase B gradient over a 5-minute period.

Liquid chromatography mass spectrometry (LCMS) data typically were obtained with an Applied Biosystems (Foster City, Calif.) Model API-150EX instrument. LCMS 10-90 data were obtained with a 10% to 90% mobile phase B gradient over a 5-minute period.

Small-scale purifications were typically conducted using an API 150EX Prep Workstation system from Applied Biosystems. The mobile phase "A" was water containing 0.05% trifluoroacetic acid (v/v); and mobile phase "B" was acetonitrile containing 0.05% trifluoroacetic acid (v/v). For small samples (about 3 to 50 mg recovered sample size), the following conditions were typically used: 20 mL/min flow rate; 15 min gradients and a 20 mm×50 mm Prism RP column with 5 micron particles (Thermo Hypersil-Keystone, Bellefonte, Pa.). For larger samples (i.e., greater than about 100 mg crude sample), the following conditions were typically used: 60 mL/min flow rate; 30 min gradients and a 41.4 mm×250 mm Microsorb BDS column with 10 micron particles (Varian, Palo Alto, Calif.).

For $^1$H NMR data, the following abbreviations are used: s=singlet, d=doublet, t=triplet, q=quartet, m=multiplet, br=broad, nd=not determined.

Example 1

Biphenyl-2-ylcarbamic Acid Piperidin-4-yl Ester

Biphenyl-2-isocyanate (97.5 g, 521 mmol) and 4-hydroxy-1-benzylpiperidine (105 g, 549 mmol) (both commercially available from Aldrich, Milwaukee, Wis.) were heated together at 70° C. for 12 h, during which time the formation of biphenyl-2-ylcarbamic acid 1-benzylpiperidin-4-yl ester was monitored by LCMS. The reaction mixture was then cooled to 50° C. and ethanol (1 L) was added, and then 6M hydrochloric acid (191 mL) was added slowly. The reaction mixture was then cooled to ambient temperature and ammonium formate (98.5 g, 1.56 mol) was added and nitrogen gas was bubbled through the solution vigorously for 20 min. Palladium (10 wt. % (dry basis) on activated carbon) (20 g) was then added. The reaction mixture was heated at 40° C. for 12 h and then filtered through a pad of Celite. The solvent was then removed under reduced pressure and 1M hydrochloric acid (40 mL) was added to the crude residue. Sodium hydroxide (10N) was then added to adjust the pH to 12. The aqueous layer was extracted with ethyl acetate (2×150 mL) and dried (magnesium sulfate), and then the solvent was removed under reduced pressure to give biphenyl-2-ylcarbamic acid piperidin-4-yl ester (155 g, 100%). HPLC (10-70) $R_t$=2.52; MS m/z: [M+H$^+$] calc'd for $C_{18}H_{20}N_2O_2$ 297.15; found 297.3.

Example 2

3-[4-(Biphenyl-2-ylcarbamoyloxy)piperidin-1-yl] propionic Acid

To a solution of biphenyl-2-ylcarbamic acid piperidin-4-yl ester (50 g, 67.6 mmol) in dichloromethane (500 mL) was added acrylic acid (15.05 mL, 100 mmol). The resulting mixture was heated at 50° C. under reflux for 18 hours and then the solvent was removed. Methanol (600 mL) was added and this mixture was heated at 75° C. for 2 hours and then cooled to room temperature to form a thick slurry. The solid was collected by filtration, washed with methanol (50 mL) and air dried to afford 3-[4-(biphenyl-2-ylcarbamoyloxy)piperidin-1-yl]propionic acid (61 g, 96% purity) as white powder.

Example 3

N-{5-[(R)-2-Amino-1-(tert-butyldimethylsilanyloxy)ethyl]-2-hydroxyphenyl}-formamide Acetic Acid Salt Step A—N-{5-[(R)-2-Benzylamino-1-(tert-butyldimethylsilanyloxy)ethyl]-2-benzyloxyphenyl}formamide To a 500 mL three-necked round-bottomed flask was added N-{2-benzyloxy-5-[(R)-2-bromo-1-(tert-butyldimethylsilanyloxy)ethyl]phenyl}formamide (100 g, 215 mmol) and N-methyl-2-pyrrolidone (300 mL). Benzylamine (69.4 mL, 648 mol) was added and the reaction mixture was flushed with nitrogen. The reaction mixture was then heated to 90° C. and stirred for about 8 hours. The reaction mixture was then cooled to room temperature and water (1.5 L) and ethyl acetate (1.5 L) were added. The layers were separated and the organic layer was washed with water (500 mL), a 1:1 mixture of water and saturated brine (500 mL total), and then again with water (500 mL). The organic layer was then dried over anhydrous magnesium sulfate, filtered and concentrated under reduced pressure to provide crude N-{5-[(R)-2-benzylamino-1-(tert-butyldimethylsilanyloxy)ethyl]-2-benzyloxyphenyl}formamide (100 g, 90% yield, 75-80% purity) as an orange-brown thick oil.

Step B—N-{5-[(R)-2-Amino-1-(tert-butyldimethyl-silanyloxy)ethyl]-2-hydroxyphenyl}formamide Acetic Acid Salt Crude N-{5-[(R)-2-benzylamino-1-(tert-butyldimethylsilanyloxy)ethyl]-2-benzyloxyphenyl}formamide (100 g, 194 mmol) was dissolved in methanol (1 L) and acetic acid (25 mL, 291 mmol). The resulting mixture was purged with dry nitrogen and then palladium hydroxide on carbon (20 g, 20 wt. %, about 50% water) was added. Hydrogen was bubbled through the reaction mixture with stirring at room temperature for about 10 hours. The mixture was then purged with dry nitrogen and the mixture was filtered through Celite. The filtrate was concentrated on a rotary evaporator and ethyl acetate (600 mL) was added to the residue. This mixture was stirred for about 2 hours at which time a thick yellow slurry had developed. The slurry was filtered and the precipitate was air dried to provide N-{5-[(R)-2-amino-1-(tert-butyldimethylsilanyloxy)ethyl]-2-hydroxyphenyl}formamide acetic acid salt (48 g, 98% purity) as a yellow-white solid. LCMS (10-70) $R_t$=3.62; [M+H$^+$] found 311.3.

Example 4

Biphenyl-2-ylcarbamic acid 1-[2-(4-{[(R)-2-(3-Formylamino-4-hydroxyphenyl)-2-hydroxyethylamino]methyl}-2,5-dimethylphenylcarbamoyl)ethyl]piperidin-4-yl Ester

Step A—Methyl 2,5-Dimethyl-4-nitrobenzoate

To a stirred solution of 2,5-dimethyl-4-nitrobenzoic acid (480 mg, 2.4 mmol) in dry methanol (8.2 mL) at 0° C. under dry nitrogen was added thionyl chloride (0.538 mL, 7.38 mmol). The resulting mixture as allowed to warm to room temperature and stirred for about 7 hours. Additional thionyl chloride (0.300 mL) was added and stirring was continued at room temperature overnight. The solvent was removed under reduced pressure and the residue was dissolved in ethyl acetate. This solution was washed with saturated aqueous sodium bicarbonate, dried over anhydrous sodium sulfate and concentrated under reduced pressure to provide methyl 2,5-dimethyl-4-nitrobenzoate (578 mg) as a pale yellow solid. HPLC (10-70) $R_t$=4.61; $^1$H NMR (300 MHz, CDCl$_3$) δ 2.57 (s, 3H), 2.61 (s, 3H), 3.94 (s, 3H), 7.82 (s, 1H), 7.87 (s, 1H).

Step B—Methyl 4-Amino-2,5-dimethylbenzoate

To a stirred solution of methyl 2,5-dimethyl-4-nitrobenzoate (523 mg, 2.5 mmol) in a 9:1 mixture of methanol and water (25 mL total) at 0° C. was added ammonium chloride (401 mg, 7.5 mmol). Zinc (1.63 g, 25 mmol) was added portionwise and the resulting mixture was stirred at room temperature overnight. The reaction mixture was then filtered through Celite and the Celite pad was washed with methanol. The filtrate was concentrated under reduced pressure and the resulting residue was dissolved in ethyl acetate. This solution was washed with saturated aqueous sodium bicarbonate, dried over anhydrous sodium sulfate and concentrated under reduced pressure to provide methyl 4-amino-2,5-dimethylbenzoate (450 mg) as a yellow oil. $^1$H NMR (300 MHz, CDCl$_3$) δ 2.14 (s, 3H), 2.53 (s, 3H), 3.83 (s, 3H), 3.85 (br s, 2H), 6.48 (s, 1H), 7.72 (s, 1H).

Step C—Methyl 4-{3-[4-(Biphenyl-2-ylcarbamoyloxy)piperidin-1-yl]propionylamino}-2,5-dimethylbenzoate To a stirred solution of 3-[4-(biphenyl-2-ylcarbamoyloxy)piperidin-1-yl]propionic acid (670 mg, 1.82 mmol) and methyl 4-amino-2,5-dimethylbenzoate (390 mg, 2.18 mmol) in dichloromethane (3.6 mL) and diisopropylethylamine (0.413 mL) was added O-(7-azabenzotriazol-1-yl)-1,1,3,3-tetramethyluronium hexafluorophosphate (HATU) (829 mg, 2.18 mmol). The resulting mixture was stirred at room temperature overnight. The mixture was then washed with saturated aqueous sodium bicarbonate, dried over anhydrous sodium sulfate, filtered and concentrated under reduced pressure. The residue was purified by silica gel chromatography eluting with dichloromethane containing from 3% to 5% methanol to provide methyl 4-{3-[4-(biphenyl-2-ylcarbamoyloxy)piperidin-1-yl]propionylamino}-2,5-dimethylbenzoate (568 mg, 59% yield). LCMS (10-70) $R_t$=4.55; [M+H$^+$] found 530.4.

Step D—Biphenyl-2-ylcarbamic acid 1-[2-(4-Hydroxymethyl-2,5-dimethylphenylcarbamoyl)ethyl]piperidin-4-yl Ester To a stirred solution of 1M lithium aluminum hydride in THF (1.52 mL, 1.52 mmol) at 0° C. was added methyl 4-{3-[4-(biphenyl-2-ylcarbamoyloxy)piperidin-1-yl]propionylamino}-2,5-dimethylbenzoate (400 mg, 0.76 mmol). The resulting mixture was stirred at 0° C. for 30 minutes and then a 1:1 mixture of 1M aqueous sodium hydroxide (5 mL) and water (5 mL) was added and stirring was continued for 2 hours. Dichloromethane was added and the organic layer was separated, dried over sodium sulfate and the solvent removed under reduced pressure. The residue was purified by silica gel chromatography eluting with dichloromethane containing 5% methanol to provide biphenyl-2-ylcarbamic acid 1-[2-(4-hydroxymethyl-2,5-dimethylphenylcarbamoyl)-ethyl]piperidin-4-yl ester. LCMS (10-70) $R_t$=3.94; [M+H$^+$] found 502.5.

Step E—Biphenyl-2-ylcarbamic acid 1-[2-(4-Formyl-2,5-dimethylphenylcarbamoyl)ethyl]piperidin-4-yl Ester To a solution of biphenyl-2-ylcarbamic acid 1-[2-(4-hydroxymethyl-2,5-dimethylphenylcarbamoyl)ethyl]piperidin-4-yl ester (151 mg, 0.3 mmol) in dichloromethane (3 mL) at 0° C. was added dimethyl sulfoxide (128 µL, 1.8 mmol) and diisopropylethylamine (157 µL, 0.9 mmol). After 15 minutes, sulfur trioxide pyridine complex (143 mg, 0.9 mmol) was added and stirring at 0° C. was continued for 1 hour. Water was added to quench the reaction and the layers were separated. The organic layer was dried over anhydrous sodium sulfate, filtered and the solvent removed under reduced pressure to give biphenyl-2-ylcarbamic acid 1-[2-(4-formyl-2,5-dimethylphenylcarbamoyl)ethyl]piperidin-4-yl ester (150 mg, 100% yield), which was used without further purification. [M+H$^+$] found 500.4.

Step F—Biphenyl-2-ylcarbamic acid 1-[2-(4-{[(R)-2-(tert-Butyldimethylsilanyloxy)-2-(3-formylamino-4-hydroxyphenyl)ethylamino]methyl}-2,5-dimethylphenylcarbamoyl)ethyl]piperidin-4-yl Ester A solution of biphenyl-2-ylcarbamic acid 1-[2-(4-formyl-2,5-dimethylphenylcarbamoyl)ethyl]piperidin-4-yl ester (150 mg, 0.30 mmol) and N-{5-[(R)-2-amino-1-(tert-butyldimethylsilanyloxy)ethyl]-2-hydroxyphenyl}formamide (112 mg, 0.36 mmol) in a 1:1 mixture of dichloromethane and methanol (3.0 mL total) was stirred at room temperature for 30 minutes. Sodium triacetoxyborohydride (191 mg, 0.9 mmol) was added and the resulting mixture was stirred at room temperature overnight. Acetic acid was added to quench the reaction and the mixture was concentrated under reduced pressure to give biphenyl-2-ylcarbamic acid 1-[2-(4-{[(R)-2-(tert-butyldimethylsilanyloxy)-2-(3-formylamino-4-hydroxyphenyl)ethylamino]methyl}-2,5-dimethylphenylcarbamoyl)-ethyl]piperidin-4-yl ester, which was used without further purification. LCMS (10-70) $R_t$=4.55; [M+H$^+$] found 794.6.

Step G—Biphenyl-2-ylcarbamic acid 1-[2-(4-{[(R)-2-(3-Formylamino-4-hydroxyphenyl)-2-hydroxyethylamino]methyl}-2,5-dimethylphenylcarbamoyl) ethyl]piperidin-4-yl Ester To a suspension of biphenyl-2-ylcarbamic acid 1-[2-(4-{[(R)-2-(tert-butyldimethylsilanyloxy)-2-(3-formylamino-4-hydroxyphenyl)ethylamino]methyl}-2,5-dimethylphenylcarbamoyl)-ethyl]piperidin-4-yl ester (238 mg, 0.30 mmol) in dichloromethane (3.0 mL) was added triethylamine trihydrofluoride (147 µL, 0.90 mmol). This mixture was stirred at room temperature overnight and then the mixture was concentrated under reduced pressure. The residue was purified by prep-RP-HPLC (gradient: 2 to 50% acetonitrile in water with 0.05% TFA). The appropriate fractions were collected and combined and lyophilized to give biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester as the ditrifluoroacetate salt (50 mg, 97% purity). LPLC (2-90) $R_t$=2.76; [M+H$^+$] found 680.8.

Example 5

Biphenyl-2-ylcarbamic acid 1-[2-(4-{[(R)-2-(3-Formylamino-4-hydroxyphenyl)-2-hydroxyethylamino]methyl}-2,5-dimethylphenylcarbamoyl) ethyl]piperidin-4-yl Ester Step A—Dibenzyl-(4-iodo-2,5-dimethylphenyl)amine To a 2-liter round-bottomed flask equipped with an overhead stirrer, temperature control and an addition funnel was added 4-iodo-2,5-dimethylaniline (100.0 g, 0.405 mol) (from Spectra Group Limited, Inc., Millbury, Ohio). Ethanol (1 L) and solid potassium carbonate (160 g, 1.159 mol) were added and then neat benzyl bromide (140 mL, 1.179 mol) was added in one portion. The resulting mixture was stirred at 30° C. for about 18 hours at which time HPLC shows greater than 98% conversion. The mixture was then cooled to room temperature and hexanes (1 L) were added. This mixture was stirred for 15 minutes and then filtered through a paper filter to removed solids and the filter cake was washed with hexanes (200 mL). Using a rotoevaporator, the volume of the filtrate was reduced to about 500 mL and concentrated hydrochloric acid (30 mL) was added. The remaining solvent was then removed using a rotoevaporator. To the resulting residue was added hexanes (500 mL) and this mixture was stirred for about 30 minutes as which time a free-flowing slurry had formed. The slurry was filtered and the filter cake was washed with hexanes (200 mL) and dried to provide dibenzyl-(4-iodo-2,5-dimethylphenyl)amine hydrochloride (115 g, 62% yield, 97.5% purity) as a greenish colored solid.

The dibenzyl-(4-iodo-2,5-dimethylphenyl)amine hydrochloride was transferred to a 3 L flask and toluene (1 L) and 1 M aqueous sodium hydroxide (1 L) were added. The resulting mixture was stirred for 1 hour and then the layer were separated. The organic layer was washed with dilute brine (500 mL) and the solvent was removed by rotoevaporation to provide dibenzyl-(4-iodo-2,5-dimethylphenyl)amine (80 g) as a semi-solid thick oil. (Alternatively, dichloromethane can be used in place of toluene in this step). $^1$H NMR (300 MHz, DMSO-d$_6$) δ 2.05 (s, 3H), 2.19 (s, 3H), 3.90 (s, 4H), 6.91 (s, 1H), 7.05-7.20 (m, 10H), 7.42 (s, 1H); MS [M+H$^+$] found 428.

Step B—4-Dibenzylamino-2,5-dimethylbenzaldehyde Hydrochloride

To a 1-liter 3-necked round-bottomed flask equipped with an overhead stirrer, temperature control and an addition funnel was added dibenzyl-(4-iodo-2,5-dimethylphenyl)amine (15 g, 35 mmol). Toluene (300 mL) was added and the resulting mixture was stirred for about 15 minutes. The reaction flask was purged with dry nitrogen and cooled to about –20° C. and 1.6 M n-butyllithium in hexanes (33 mL, 53 mmol) was added dropwise via the addition funnel. During the addition, the internal temperature of the reaction mixture was maintained below –10° C. When the addition was complete, the resulting mixture was stirred at about –15° C. for 15 minutes. N,N-Dimethylformamide (10 mL, 129 mmol) was then added dropwise while maintaining the internal reaction temperature below 0° C. The resulting mixture was then stirred at –20° C. to 0° C. for about 1 hour. Aqueous 1 M hydrochloric acid (200 mL) was then added over a 5 minute period and the resulting mixture was stirred for 15 minutes. The layers were then separated and the organic layer was washed with dilute brine (100 mL). The organic layer was then dried over anhydrous sodium sulfate, filtered and the solvent removed under reduced pressure to provide 4-dibenzylamino-2,5-dimethylbenzaldehyde hydrochloride (11.5 g, 90% yield, 95% purity) as thick oil that solidified upon standing. The product contained about 3 to 5% of the des-iodo by-product. $^1$H NMR (300 MHz, CDCl$_3$) δ 2.42 (s, 3H), 2.50 (s, 3H), 4.25 (s, 4H), 6.82 (s, 1H), 7.10-7.30 (10H, m), 7.62 (1H, s), 10.15 (1H, s); MS [M+H$^+$] found 330.3.

Step C—4-[1,3]Dioxolan-2-yl-2,5-dimethylphenylamine

To a 500 mL round-bottomed flask was added 4-dibenzylamino-2,5-dimethylbenzaldehyde hydrochloride (11.5 g, 31.4 mmol) and toluene (150 mL) and the resulting mixture was stirred until the salt completely dissolved. The reaction flask was then purged with dry nitrogen for 5 minutes. Ethylene glycol (5.25 mL, 94.2 mmol) and p-toluenesulfonic acid (760 mg, 6.2 mmol) were added and the resulting mixture was heated at 60° C. to 80° C. for about 20 hours. The solvent was then removed slowly (over about 40 minutes) at 40° C. on a rotary evaporator. Toluene (100 mL) was added to the residue and the solvent was again removed slowly at 40° C. on a rotary evaporator. This process was repeated using another aliquot of toluene (100 mL) and the mixture was evaporated to dryness. Ethyl acetate (150 mL) and saturated aqueous sodium bicarbonate (100 mL) were added to the residue and the layers were separated. The organic layer was washed with brine (50 mL) and then dried over anhydrous sodium sulfate, filtered and concentrated under reduced pressure to provide crude dibenzyl-(4-[1,3]dioxolan-2-yl-2,5-dimethyl-phenyl)amine (11.4 g).

The crude dibenzyl-(4-[1,3]dioxolan-2-yl-2,5-dimethylphenyl)amine was dissolved in a 2:1 mixture of ethanol and water (150 mL total) and the resulting mixture was purged with dry nitrogen for 5 minutes. Palladium on carbon (2.3 g, 10 wt. % containing about 50% water) and solid sodium bicarbonate (1.0 g) were added and the resulting mixture was hydrogenated at about 1 atm of hydrogen at 25° C. to 30° C. for about 8 hours. The mixture was then filtered through Celite and the filtrate was concentrated on a rotary evaporator to provide crude 4-[1,3]dioxolan-2-yl-2,5-dimethylphenylamine (5.6 g, 92% yield) as a thick oil. $^1$H NMR (300 MHz, DMSO-$d_6$) δ 2.05 (s, 3H), 2.22 (s, 3H), 3.7-3.9 (m, 4H), 3.95 (s, 4H), 5.59 (s, 1H), 6.72 (s, 1H), 7.0-7.25 (m, 11H).

Step D—N-(4-[1,3]Dioxolan-2-yl-2,5-dimethylphenyl)acrylamide

To a 500 mL round-bottom flask was added crude 4-[1,3]dioxolan-2-yl-2,5-dimethylphenylamine (5.6 g, 29 mmol), dichloromethane (100 mL) and diisopropylethylamine (7.6 mL, 43.5 mmol). The resulting mixture was stirred at room temperature until the ingredients dissolved and then the mixture was cooled to 0° C. Acryloyl chloride (2.35 mL, 29 mmol) was then added dropwise over a 5 minute period. The reaction mixture was stirred at 0° C. to 5° C. for 1 hour and then water (50 mL) was added and stirring was continued for about 30 minutes at which time fine solids had formed. The mixture was filtered to collect the solids. The layers of the filtrate were then separated and the organic layer was concentrated under reduced pressure to dryness. Dichloromethane (50 mL) was added to the residue and this mixture was stirred until a free-flowing slurry developed. The slurry was filtered (using the same funnel used to collect the fine solids above) and the filter cake was washed with dichloromethane (10 mL) and dried to provide N-(4-[1,3]dioxolan-2-yl-2,5-dimethylphenyl)acrylamide (3.1 g, 97% purity) as a white to off-white solid.

The filtrate from above was then evaporated to dryness and methanol (10 mL) was added to the residue. This mixture was stirred for 15 minutes and then the precipitate was collected by filtration, washed with methanol (5 mL) and dried to give a second crop of N-(4-[1,3]dioxolan-2-yl-2,5-dimethylphenyl)acrylamide (0.8 g, 95% purity). $^1$H NMR (300 MHz, CD$_3$OD) δ 2.10 (s, 3H), 2.23 (s, 3H), 3.85-4.10 (m, 4H), 5.60-6.40 (m, 3H), 5.59 (s, 1H), 7.18 (s, 1H), 7.23 (s, 1H).

Step E—Biphenyl-2-ylcarbamic acid 1-[2-(4-Formyl-2,5-dimethylphenylcarbamoyl)ethyl]piperidin-4-yl Ester Hydrochloride To a 50 mL round-bottom flask was added biphenyl-2-ylcarbamic acid piperidin-4-yl ester (1.2 g, 4.04 mmol) and N-(4-[1,3]dioxolan-2-yl-2,5-dimethylphenyl)acrylamide (1.0 g, 4.04 mmol). Ethanol (10 mL) and dichloromethane (10 mL) were added to form a slurry. The reaction mixture was heated at 45° C. to 50° C. for about 18 hours and then cooled to room temperature. Aqueous 1M hydrochloric acid (10 mL) was added and the resulting mixture was stirred vigorously for about 3 hours. Dichloromethane (10 mL) was added and the resulting mixture was stirred for about 5 minutes. The layers were then separated and the organic layer was dried over anhydrous sodium sulfate, filtered and concentrated on a rotary evaporator to provide crude biphenyl-2-ylcarbamic acid 1-[2-(4-formyl-2,5-dimethylphenylcarbamoyl)ethyl]piperidin-4-yl ester hydrochloride (1.9 g). $^1$H NMR (300 MHz, DMSO-$d_6$) δ 1.2-1.4 (m, 2H), 1.58-1.75 (m, 2H), 2.0-2.17 (m, 2H), 2.19 (s, 3H), 2.38 (s, 3H), 2.41-2.50 (m, 4H), 2.5-2.75 (m, 2H), 4.31-4.42 (m, 1H), 7.10-7.35 (m, 9H), 7.55 (s, 1H), 7.75 (s, 1H), 8.59 (s, 1H), 9.82 (s, 1H), 9.98 (s, 1H); MS [M+H$^+$] found 500.2.

Step F—Biphenyl-2-ylcarbamic acid 1-[2-(4-{[(R)-2-(tert-Butyldimethylsilanyloxy)-2-(3-formylamino-4-hydroxyphenyl)ethylamino]methyl}-2,5-dimethylphenyl-carbamoyl)ethyl]piperidin-4-yl Ester To a 2 L three-necked round-bottom flask was added biphenyl-2-ylcarbamic acid 1-[2-(4-formyl-2,5-dimethylphenylcarbamoyl)ethyl]piperidin-4-yl ester hydrochloride (38 g, 70 mmol) and N-{5-[(R)-2-amino-1-(tert-butyldimethylsilanyloxy)ethyl]-2-hydroxyphenyl}formamide acetic acid salt (33.6 g, 91 mmol). Dichloromethane (500 mL) and methanol (500 mL) were added and the resulting mixture was stirred at room temperature under dry nitrogen for about 3 hours. The reaction mixture was then cooled to 0° C. to 5° C. and solid sodium triacetoxyborohydride (44.5 g, 381 mmol) was added in portions over a 10 minute period. The reaction mixture was slowly warmed from 0° C. to room temperature over a period of about 2 hours and then cooled to 0° C. Saturated aqueous sodium bicarbonate (500 mL) and dichloromethane (500 mL) were added. This mixture was stirred thoroughly and then the layers were separated. The organic layer was washed with brine (500 mL), dried over anhydrous sodium sulfate, filtered and concentrated under reduced pressure to give crude biphenyl-2-ylcarbamic acid 1-[2-(4-{[(R)-2-(tert-butyldimethylsilanyloxy)-2-(3-formylamino-4-hydroxyphenyl)ethylamino]methyl}-2,5-dimethylphenylcarbamoyl)-ethyl]piperidin-4-yl ester (55 g, 86% purity) as a yellow solid.

The crude product (30 g) was dissolved in dichloromethane containing 2% methanol (150 mL total) and loaded onto a silica gel column (300 g) that had been packed and equilibrated with dichloromethane containing 2% methanol and 0.5% ammonium hydroxide. The product was eluted from the column using dichloromethane containing 2% methanol and 0.5% ammonium hydroxide (1 L); dichloromethane containing 4% methanol and 0.5% ammonium hydroxide (1 L) and dichloromethane containing 5% methanol and 0.5% ammonium hydroxide (about 3 L). Fractions (200 mL) were collected and those fractions having a purity greater than 90% were combined and concentrated under reduced pressure to provide biphenyl-2-ylcarbamic acid 1-[2-(4-{[(R)-2-(tert-butyldimethylsilanyloxy)-2-(3-formylamino-4-hydroxyphenyl)ethylamino]methyl}-2,5-dimethylphenylcarbamoyl)-ethyl]piperidin-4-yl ester (21.6 g, 96.5% purity) as a yellowish solid. MS [M+H$^+$] found 794.6.

Step G—Biphenyl-2-ylcarbamic acid 1-[2-(4-{[(R)-2-(3-Formylamino-4-hydroxyphenyl)-2-hydroxyethylamino]methyl}-2,5-dimethylphenyl-carbamoyl)ethyl]piperidin-4-yl Ester Hydrofluoride Salt To a 1 L round-bottom flask was added biphenyl-2-ylcarbamic acid 1-[2-(4-{[(R)-2-(tert-butyldimethylsilanyloxy)-2-(3-formylamino-4-hydroxyphenyl)ethylamino]methyl}-2,5-dimethylphenylcarbamoyl)ethyl]piperidin-4-yl ester (21.5 g, 27.1 mmol) and dichloromethane (200 mL). The resulting mixture was stirred at room temperature until the ingredients dissolved and then triethylamine trihydrofluoride (8.85 mL, 54.2 mmol) was added and the resulting mixture was stirred at 25° C. for about 48 hours. The solvent was removed on a rotary evaporator to provide a thick paste. Dichloromethane (100 mL) and ethyl acetate (200 mL) were added to the paste and the resulting mixture was stirred for 30 minutes. The resulting slurry was slowly filtered under dry nitrogen and the filter cake was washed with a 1:2 mixture of dichloromethane and ethyl acetate (100 mL total), dried under nitrogen for 2 hours and then dried under vacuum overnight to provide biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester as a hydrofluoride salt (25 g, 96.9% purity) which was a hard clay-like solid. MS [M+H$^+$] found 680.8.

Step H—Biphenyl-2-ylcarbamic acid 1-[2-(4-{[(R)-2-(3-Formylamino-4-hydroxyphenyl)-2-hydroxyethylamino]methyl}-2,5-dimethylphenylcarbamoyl)-ethyl]piperidin-4-yl Ester Biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester hydrofluoride salt (25 g) was purified on a 6-inch reverse-phase column (Microsorb solid phase) in three equal batches using a 10% to 50% mixture of acetonitrile in water containing 1% trifluoroacetic acid as the mobile phase. Fractions with greater than 99% purity were combined and then diluted with one volume of water. The resulting mixture cooled to 0° C. and solid sodium bicarbonate was added until the pH of the mixture was about 7.5 to 8.0. Within about 5 minutes, a white slurry developed. The slurry was stirred for 30 minutes and then filtered. The filter cake was washed with water (500 mL), air dried for about 4 hours and then dried in vacuum overnight to provide biphenyl-2-ylcarbamic acid 1-[2-(4-{[(R)-2-(3-formylamino-4-hydroxyphenyl)-2-hydroxyethylamino]methyl}-2,5-dimethylphenyl-carbamoyl)ethyl]piperidin-4-yl ester (12 g, 99+% purity), as a semi-crystalline free base.

Example 6

Biphenyl-2-ylcarbamic Acid 1-[2-(4-{[(R)-2-(3-Formylamino-4-hydroxyphenyl)-2-hydroxyethylamino]methyl}-2,5-dimethylphenylcarbamoyl)ethyl]piperidin-4-yl Ester Step A—Biphenyl-2-ylcarbamic Acid 1-[2-(4-[1,3] Dioxolan-2-yl-2,5-dimethylphenylcarbamoyl)ethyl]piperidin-4-yl Ester To a 500 mL round-bottom flask was added biphenyl-2-ylcarbamic acid piperidin-4-yl ester (17.0 g, 58 mmol) and N-(4-[1,3]dioxolan-2-yl-2,5-dimethylphenyl)acrylamide (13.1 g, 52.9 mmol). Ethanol (150 mL) and dichloromethane (150 mL) were added to form a slurry. The reaction mixture was heated at 50° C. to 55° C. for about 24 hours and then cooled to room temperature. Most of the solvent was removed on a rotary evaporator, resulting in a thick slurry. Ethanol (reagent grade) was added to form a total volume of about 200 mL and the resulting mixture was heated to 80° C. and then cooled slowly to room temperature. The resulting thick white slurry was filtered, washed with ethanol (20 mL) and dried in vacuum to provide biphenyl-2-ylcarbamic acid 1-[2-(4-[1,3] dioxolan-2-yl-2,5-dimethylphenylcarbamoyl)ethyl]piperidin-4-yl ester (23.8 g, about 98% purity) as a white solid.

Step B—Biphenyl-2-ylcarbamic Acid 1-[2-(4-Formyl-2,5-dimethylphenyl-carbamoyl)ethyl]piperidin-4-yl Ester To a 500 mL round-bottom flask was added biphenyl-2-ylcarbamic acid 1-[2-(4-[1,3]dioxolan-2-yl-2,5-dimethylphenylcarbamoyl)ethyl]piperidin-4-yl ester (15 g, 27.6 mmol) and acetonitrile (150 mL) to form a slurry. Aqueous 2 M hydrochloric acid (75 mL) was added and the resulting mixture was stirred at 30° C. for 1 hour. The mixture was then cooled to room temperature and ethyl acetate (150 mL) was added. Aqueous 2 M sodium hydroxide (75 mL) was added, the pH was checked and then additional 2 M sodium hydroxide was added until the pH of the solution was in the range of 9 to 10. The layers were separated and the organic layer was washed with diluted brine (75 mL; 1:1 brine/water), dried over anhydrous sodium sulfate and the solvent removed on a rotary evaporator to give biphenyl-2-ylcarbamic acid 1-[2-(4-formyl-2,5-dimethylphenyl-carbamoyl)ethyl]piperidin-4-yl ester (12.5 g, about 98% purity). If desired, the purity of this intermediate can be increased by forming a slurry with ethanol (3 volumes of ethanol), heating the slurry to 80° C., and then cooling slowly to room temperature and isolating by filtration.

Step C—Biphenyl-2-ylcarbamic Acid 1-[2-(4-{[(R)-2-(tert-Butyldimethylsilanyloxy)-2-(3-formylamino-4-hydroxyphenyl)ethylimino]methyl}-2,5-dimethylphenylcarbamoyl)ethyl]piperidin-4-yl Ester To a 250 mL round-bottom flask was added biphenyl-2-ylcarbamic acid 1-[2-(4-formyl-2,5-dimethylphenylcarbamoyl)ethyl]piperidin-4-yl ester (7.1 g, 14.2 mmol) and N-{5-[(R)-2-amino-1-(tert-butyldimethylsilanyloxy)ethyl]-2-hydroxyphenyl}formamide acetic acid salt (5.8 g, 15.6 mmol). Methanol (100 mL) was added to form a slurry and this mixture was stirred at 45° C. to 50° C. under nitrogen for 1 hour. The mixture was then cooled to room temperature and toluene (50 mL) was added and the solvent was removed on a rotary evaporator at temperature ranging from 35° C. to 45° C. Toluene (50 mL) was added to the residue and the solvent was removed to provide biphenyl-2-ylcarbamic acid 1-[2-(4-{[(R)-2-(tert-butyldimethylsilanyloxy)-2-(3-formylamino-4-hydroxyphenyl)ethylimino]methyl}-2,5-dimethyl-phenyl-carbamoyl)ethyl]piperidin-4-yl ester (12 g) as a yellow-orange solid.

Step D—Biphenyl-2-ylcarbamic Acid 1-[2-(4-{[(R)-2-(tert-Butyldimethylsilanyloxy)-2-(3-formylamino-4-hydroxyphenyl)ethylamino]methyl}-2,5-dimethylphenyl-carbamoyl)ethyl]piperidin-4-yl Ester To a hydrogenation flask was added biphenyl-2-ylcarbamic acid 1-[2-(4-{[(R)-2-(tert-butyldimethylsilanyloxy)-2-(3-formylamino-4-hydroxyphenyl)ethylimino]methyl}-2,5-dimethyl-phenylcarbamoyl)ethyl]piperidin-4-yl ester (4.6 g) and 2-methyltetrahydrofuran (50 mL). The resulting mixture was stirred until the solid dissolved (about 5 min.) and then the mixture was purged with nitrogen. Platinum on carbon (920 mg, 5 wt. %, support activated carbon) was added and the mixture was hydrogenated at 50 psi (Parr shaker) for 6 hours. The mixture was then filtered through Celite and the Celite was washed with 2-methyltetrahyrofuran (10 mL). To the filtrate was added a thiopropyl-modified silica gel (20% of weight of solution, Silicycle) and this mixture was stirred at 25° C. to 30° C. for 3 hours. The mixture was then filtered through Celite and concentrated to remove the solvent. The residue was dissolved in methanol (5 mL per gram of residue) and then the resulting solution was added slowly to a vigorously stirred 1:1 mixture of saturated aqueous sodium bicarbonate and water (40 mL per gram of residue). The resulting off-white slurry was stirred for 20 minutes and then filtered. The filter cake was washed with water (20 volumes), air dried for 3 hours and then dried in vacuum at room temperature overnight to provide biphenyl-2-ylcarbamic acid 1-[2-(4-{[(R)-2-(tert-butyldimethylsilanyloxy)-2-(3-formylamino-4-hydroxyphenyl)ethylamino]methyl}-2,5-dimethylphenyl-carbamoyl)ethyl]piperidin-4-yl ester (80% recovery, about 96% purity).

Step E—Biphenyl-2-ylcarbamic Acid 1-[2-(4-{[(R)-2-(3-Formylamino-4-hydroxyphenyl)-2-hydroxy-ethylamino]methyl}-2,5-dimethylphenyl-carbamoyl) ethyl]piperidin-4-yl Ester L-Tartrate Salt To a 200 mL round-bottom flask was added biphenyl-2-ylcarbamic acid 1-[2-(4-{[(R)-2-(tert-butyldimethylsilanyloxy)-2-(3-formylamino-4-hydroxyphenyl)ethylamino]-methyl}-2,5-dimethylphenylcarbamoyl)ethyl]piperidin-4-yl ester (3.8 g, 4.8 mmol) and 2-methyltetrahydrofuran (40 mL). The resulting mixture was stirred at room temperature until the ingredients dissolved (about 15 min.) and then triethylamine trihydrofluoride (0.94 mL, 5.76 mmol) was added and the resulting mixture was stirred at 25° C. for about 24 hours. To this mixture was added a 1:1 mixture of saturated aqueous sodium bicarbonate and water (40 mL) and 2-methyltetrahydrofuran and the resulting mixture was stirred until the solid dissolved (solution pH about 8). The layers were separated and the organic layer was washed with brine (30 mL), dried over anhydrous sodium sulfate, filtered and concentrated on a rotary evaporator. The residue was dissolved in 2-methyltetrahydrofuran (50 mL) and sold L-tartaric acid (650 mg) was added. The resulting mixture was stirred at 25° C. to 30° C. for 18 hours and then filtered through filter paper. The filter cake was washed with 2-methyltetrahydrofuran (10 mL), isopropanol (10 mL) and immediately put under vacuum to provide biphenyl-2-ylcarbamic acid 1-[2-(4-{[(R)-2-(3-formylamino-4-hydroxyphenyl)-2-hydroxyethylamino]methyl}-2,5-dimethylphenyl-carbamoyl)ethyl]piperidin-4-yl ester L-tartaric acid salt (3.7 g, >97% purity).

Step F—Biphenyl-2-ylcarbamic Acid 1-[2-(4-{[(R)-2-(3-Formylamino-4-hydroxyphenyl)-2-hydroxy-ethylamino]methyl}-2,5-dimethylphenylcarbamoyl)-ethyl]piperidin-4-yl Ester To a 250 mL round-bottom flask was added biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester L-tartaric acid salt (3.5 g) and methanol (35 mL) and the resulting mixture was stirred for 15 min. A 1:1 mixture of saturated aqueous sodium bicarbonate and water (70 mL) was added over a 5 min. period and stirring was continued for 2 hours. The resulting off-white slurry was filtered and the filter cake was washed with water (20 mL), air dried for 2 hours and then dried in a vacuum overnight to provide biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)-ethyl]piperidin-4-yl ester (2.3 g) as a semi-crystalline free base.

$^1$H and $^{13}$C NMR spectra were obtained for a sample of biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)-ethyl]piperidin-4-yl ester (22.2 mg in about 0.75 mL of DMSO-$d_6$) at ambient temperature using a JEOL ECX-400 NMR spectrometer:

$^1$H NMR (400 MHz, DMSO-$d_6$), major isomer, δ 9.64 (br, 1H), 9.54 (br s, 1H), 9.43 (s, 1H), 8.67 (s, 1H), 8.26 (s, 1H), 8.03 (d, J=1.9, 1H), 7.25-7.45 (m, 9H), ~7.3 (nd, 1H), 7.07 (s, 1H), 6.88 (dd, J=8.2, 1.9, 1H), 6.79 (d, J=8.2, 1H), 5.15 (br, 1H), 4.53 (dd, J=7.3, 4.7, 1H), 4.47 (m, 1H), ~3.65 and ~3.60 (AB pair, 2H), 2.68 (br m, 2H), ~2.59 (nd, 4H), 2.44 (br t, J=6.5, 2H), 2.20 (s, 3H), ~2.17 (br m, 2H), 2.14 (s, 3H), 1.73 (br, 2H), 1.44 (br q, J=~9.0, 2H).

$^1$H NMR (400 MHz, DMSO-$d_6$), minor isomer, δ 9.64 (br, 1H), 9.43 (s 1H), 9.26 (br d, J=~7.0, 1H), 8.67 (s, 1H), 8.50 (br d, J=~7.0, 1H), 7.25-7.45 (m, 9H), ~7.3 (nd, 1H), 7.07 (s, 1H), ~7.07 (nd, 1H), 6.95 (dd, J=8.3, 1.8, 1H), 6.83 (d, J=8.3, 1H), 5.15 (br, 1H), 4.47 (m, 1H), ~3.65 and ~3.60 (AB pair, 2H), 2.68 (br m, 2H), ~2.59 (nd, 2H), 2.44 (br t, J=6.5, 2H), 2.20 (s, 3H), ~2.17 (br m, 2H), 2.14 (s, 3H), 1.73 (br, 2H), 1.44 (br q, J=~9.0, 2H).

$^{13}$C NMR (100 MHz, DMSO-$d_6$), major isomer, δ 170.0, 159.9, 153.9, 145.5, 139.3, 137.6, 135.2, 135.0, 134.8, 133.4, 133.4, 130.2, 130.2, 128.6, 128.2, 127.8, 127.4, 127.2, 127.0, 126.1, 125.7, 125.6, 121.7, 118.6, 114.5, 71.4, 70.0, 57.4, 53.9, 50.3, 50.1, 33.7, 30.7, 18.2, 17.5.

$^{13}$C NMR (100 MHz, DMSO-$d_6$), minor isomer, δ 170.0, 163.4, 153.9, 147.8, 139.3, 137.6, 135.7, 135.2, 135.0, 134.8, 133.4, 133.4, 130.2, 130.2, 128.6, 128.2, 127.8, 127.4, 127.2, 127.0, 126.1, 125.7, 123.0, 119.6, 115.6, 71.0, 70.0, 57.3, 53.9, 50.3, 50.1, 33.7, 30.7, 18.2, 17.5.

The $^1$H and $^{13}$C NMR spectra showed the presence of a major isomer (about 82 mole percent) and a minor isomer (about 18 mole percent) believed to be rotational isomers resulting from hindered rotation about the —NH—C(O)H bond. The phenyl group is believed to be syn to the carbonyl oxygen in the major isomer and anti in the minor isomer.

Example 7

Biphenyl-2-ylcarbamic Acid 1-[2-(4-Formyl-2,5-dimethylphenylcarbamoyl)ethyl]-piperidin-4-yl Ester

Step A—4-Iodo-2,5-dimethylphenylamine

To a solution of 2,5-dimethylaniline (20 g, 165 mmol) in a 1:1 mixture of dichloromethane and methanol (400 mL) was added sodium bicarbonate (20.8 g, 250 mmol) and tetramethylammonium dichloroiodate(I) (44.7 g, 165 mmol). The resulting mixture was stirred at room temperature for 1 hour and then water was added (500 mL). The organic layer was removed and washed with 5% aqueous sodium thiosulfate (500 mL) and brine (500 mL). The organic layer was then dried over anhydrous magnesium sulfate, filtered and concentrated under vacuum to provide 4-iodo-2,5-dimethylphenylamine (39.6 g, 98% yield). The product was used without further purification.

Step B—N-(4-Iodo-2,5-dimethylphenyl)acrylamide

To a solution of 4-iodo-2,5-dimethylphenylamine (37.2 g, 151 mmol) in dichloromethane (500 mL) was added sodium bicarbonate (25.4 g, 302 mmol). The resulting mixture was cooled to 0° C. and acryolyl chloride (12.3 mL, 151 mmol) was added slowly over a period of 25 minutes. The resulting mixture was stirred at room temperature overnight and then filtered. The volume of the filtrate was reduced to about 100 mL and a precipitate formed. The precipitate was filtered, dried, washed with water (1 L) and then dried again to afford N-(4-iodo-2,5-dimethylphenyl)acrylamide (42.98 g, 95% purity, 90% yield). The product was used without further purification.

Step C—Biphenyl-2-ylcarbamic Acid 1-[2-(4-Iodo-2,5-dimethylphenylcarbamoyl)-ethyl]piperidin-4-yl Ester To a solution of N-(4-iodo-2,5-dimethylphenyl)acrylamide (32.2 g, 107 mmol) in a 6:1 v/v mixture of N,N-dimethylformamide and isopropanol (700 mL) was added biphenyl-2-ylcarbamic acid piperidin-4-yl ester (36.3 g, 123 mmol). The resulting mixture was heated at 50° C. for 24 hours and then at 80° C. for 24 hours. The reaction mixture was then cooled to room temperature and concentrated under vacuum. The residue was dissolved in dichloromethane (1 L) and this solution was washed with 1N aqueous hydrochloric acid (500 mL), water (500 mL), brine (500 mL) and saturated aqueous sodium bicarbonate solution (500 mL). The organic layer was then dried over anhydrous magnesium sulfate and filtered. Ethanol (400 mL) was added and the resulting mixture was concentrated under vacuum to a volume of about 400 mL, at which time a precipitate had formed. The precipitate was filtered and dried to afford biphenyl-2-ylcarbamic acid 1-[2-(4-iodo-2,5-dimethylphenylcarbamoyl)ethyl]piperidin-4-yl ester (59.6 g, 84% purity, 79% yield). m/z: [M+H$^+$] calcd for $C_{29}H_{32}IN_3O_3$ 598.49; found 598.5.

Step D—4-{3-[4-(Biphenyl-2-ylcarbamoyloxy)piperidin-1-yl]propionylamino}-2,5-dimethylbenzoic Acid Methyl Ester To a solution of biphenyl-2-ylcarbamic acid 1-[2-(4-iodo-2,5-dimethylphenylcarbamoyl)ethyl]piperidin-4-yl ester (56 g, 94 mmol) in a 5:1 v/v mixture of N,N-dimethylformamide and methanol 600 mL) were added diisopropylethylamine (49 mL, 281 mmol), 1,3-bis(diphenylphosphino)propane (3.9 g, 9.4 mmol) and palladium(II) acetate (2.1 g, 9.4 mmol). The resulting mixture was purged with carbon monoxide and then stirred overnight at 70° C. to 80° C. under a carbon monoxide atmosphere (balloon pressure). The reaction mixture was concentrated under vacuum and the residue was dissolved in dichloromethane (500 mL). This mixture was washed with 1N aqueous hydrochloric acid (500 mL), water (500 mL) and then brine (500 mL). The organic layer was then dried over anhydrous magnesium sulfate, filtered and then concentrated under vacuum. The residue was mixed with ethanol (about 5:1 v/w ethanol to residue) and the mixture was heated until all solid material dissolved. This solution was allowed to slowly cool to room temperature and the resulting precipitate was isolated by filtration to afford 4-{3-[4-(biphenyl-2-ylcarbamoyloxy)piperidin-1-yl]propionylamino}-2,5-dimethylbenzoic acid methyl ester (47.3 g, 97% purity, 92% yield). m/z: [M+H$^+$] calcd for $C_{31}H_{35}N_3O_5$ 530.63; found 530.4.

Step E—Biphenyl-2-ylcarbamic Acid 1-[2-(4-Hydroxymethyl-2,5-dimethyl-phenylcarbamoyl)ethyl]piperidin-4-yl Ester To a solution of 4-{3-[4-(biphenyl-2-ylcarbamoyloxy)piperidin-1-yl]propionylamino}-2,5-dimethylbenzoic acid methyl ester (49.8 g, 93.9 mmol) in tetrahydrofuran (200 mL) was cooled to 0° C. and lithium aluminum hydride (10.7 g, 281.7 mmol) added portion-wise (10×1.07 g). The resulting mixture was stirred for 3 hours and then water (10.7 mL) was added, followed by 1N aqueous sodium hydroxide (10.7 mL) and additional water (32.1 mL). This mixture was stirred overnight and then filtered. The organic layer was concentrated under vacuum and the residue was mixed with ethyl acetate (about 5:1 v/w ethyl acetate to residue). This mixture was heated until all the solid material dissolved and then the solution was allowed to cool to room temperature. The resulting precipitate was filtered and dried to afford biphenyl-2-ylcarbamic acid 1-[2-(4-hydroxymethyl-2,5-dimethylphenylcarbamoyl)ethyl]piperidin-4-yl ester (24.6 g, 95% purity, 47.5% yield). This material was used without further purification. m/z: [M+H$^+$] calcd for $C_{30}H_{35}N_3O_4$ 502.62; found 502.5.

Step F—Biphenyl-2-ylcarbamic Acid 1-[2-(4-Formyl-2,5-dimethylphenylcarbamoyl)ethyl]piperidin-4-yl Ester To a solution of biphenyl-2-ylcarbamic acid 1-[2-(4-hydroxymethyl-2,5-dimethylphenylcarbamoyl)ethyl]piperidin-4-yl ester (5.0 g, 10 mmol) in dichloromethane (200 mL) was added diisopropylethylamine (8.7 mL, 50 mmol) and dimethylsulfoxide (5.6 mL, 100 mmol). The resulting mixture was cooled to 0° C. and sulfur trioxide pyridine complex (8.0 g, 50 mmol) was added. The reaction mixture was stirred for 1 hour at 0° C. and then water (300 mL) was added. The organic layer was removed and washed with 1N aqueous hydrochloric acid (300 mL) and brine (300 mL). The organic layer was then dried over anhydrous magnesium sulfate and filtered. The resulting solution containing biphenyl-2-ylcarbamic acid 1-[2-(4-formyl-2,5-dimethylphenylcarbamoyl)ethyl]piperidin-4-yl ester was used without further purification. m/z: [M+H$^+$] calcd for $C_{30}H_{33}N_3O_4$ 500.60; found 500.4.

Example 8

Figure 7:
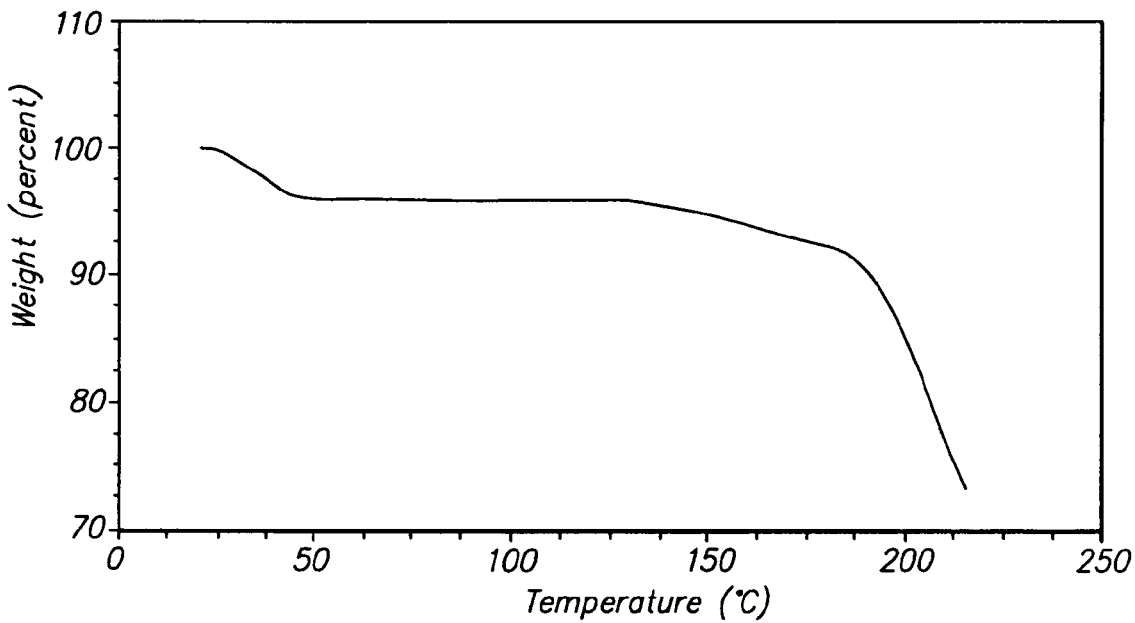
FIGS. 7, 8 and 9 show thermal gravimetric analysis (TGA) traces for Forms I, II and III, respectively, of the crystalline free base of biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester.

Preparation of Form I of Biphenyl-2-ylcarbamic acid 1-[2-(4-{[(R)-2-(3-Formylamino-4-hydroxyphenyl)-2-hydroxyethylamino]methyl}-2,5-dimethylphenylcarbamoyl)ethyl]piperidin-4-yl Ester A slurry of biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)-ethyl]piperidin-4-yl ester (55 mg) in acetonitrile (2 mL) was prepared and stirred at ambient temperature for 2 days. The solvent was removed by filtration, and the solids were dried at ambient temperature to provide Form I (50 mg). The PXRD, DSC and TGA spectra for this crystalline free base form are shown in FIGS. 1, 4 and 7, respectively.

Example 9

Figure 2:
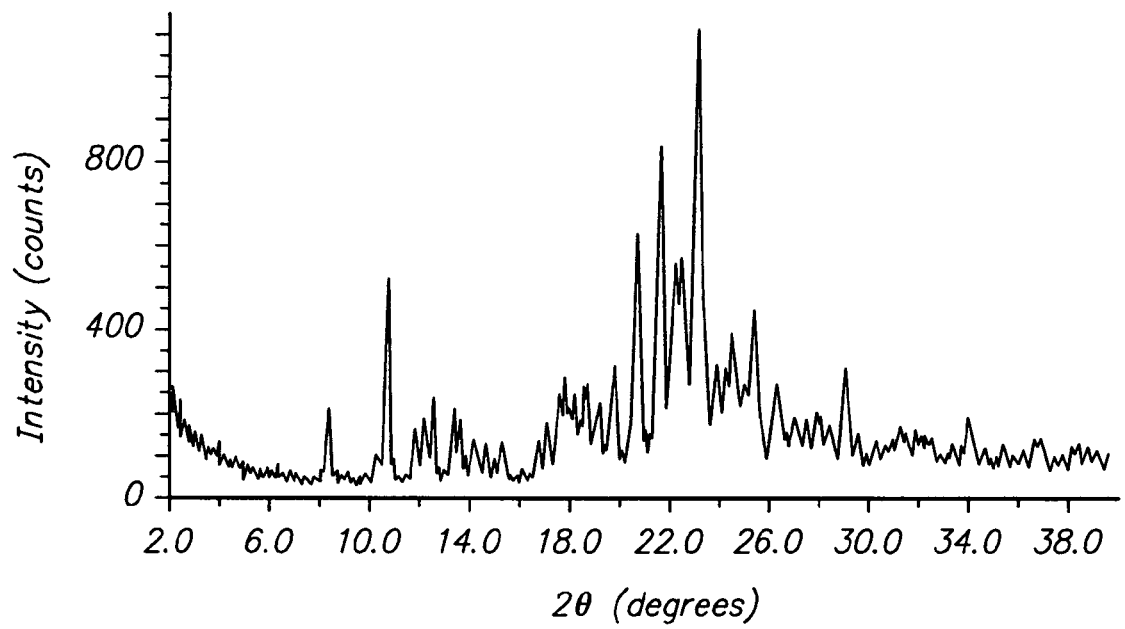
Figure 5:
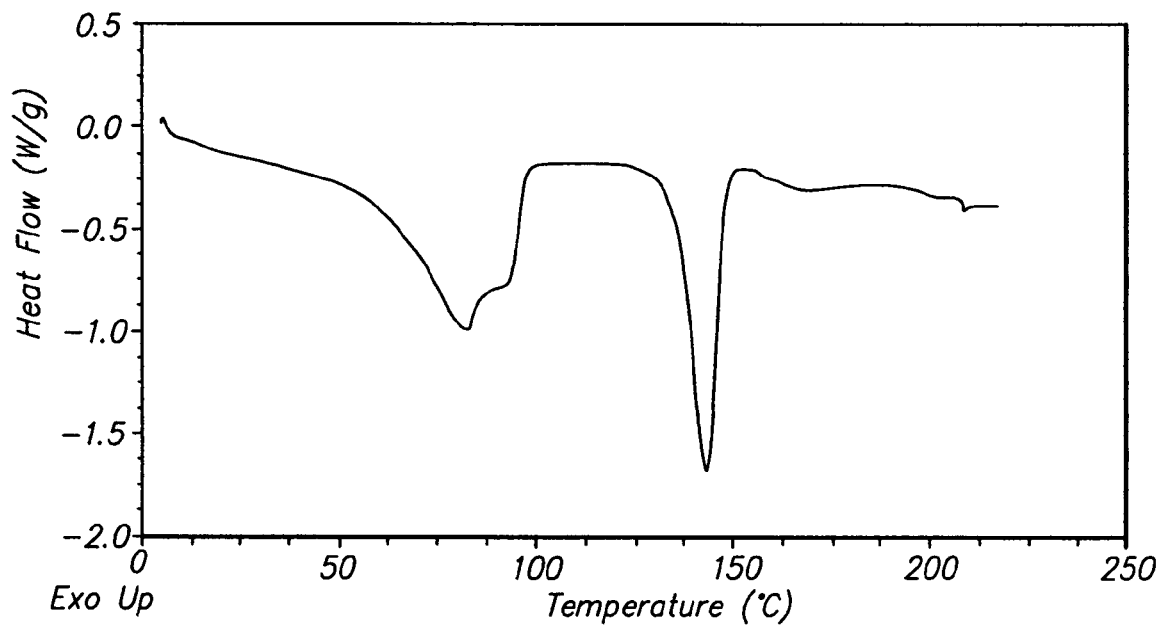
Figure 8:
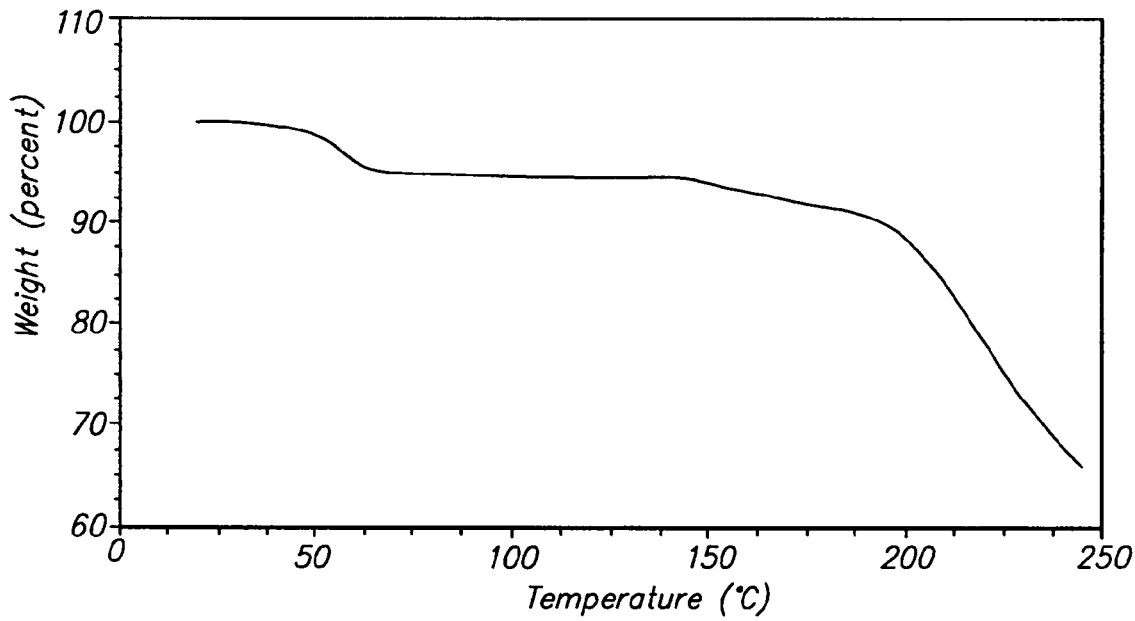

Preparation of Form II of Biphenyl-2-ylcarbamic acid 1-[2-(4-{[(R)-2-(3-Formylamino-4-hydroxyphenyl)-2-hydroxyethylamino]methyl}-2,5-dimethylphenylcarbamoyl)ethyl]piperidin-4-yl Ester A slurry of biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)-ethyl]piperidin-4-yl ester (46 mg) in isopropanol (2 mL) was prepared and stirred at ambient temperature for 2 days. The solvent was removed by filtration, and the solids were dried at ambient temperature to provide Form II (43 mg). The PXRD, DSC and TGA spectra for this crystalline free base form are shown in FIGS. 2, 5 and 8, respectively.

Example 10

Figure 3:
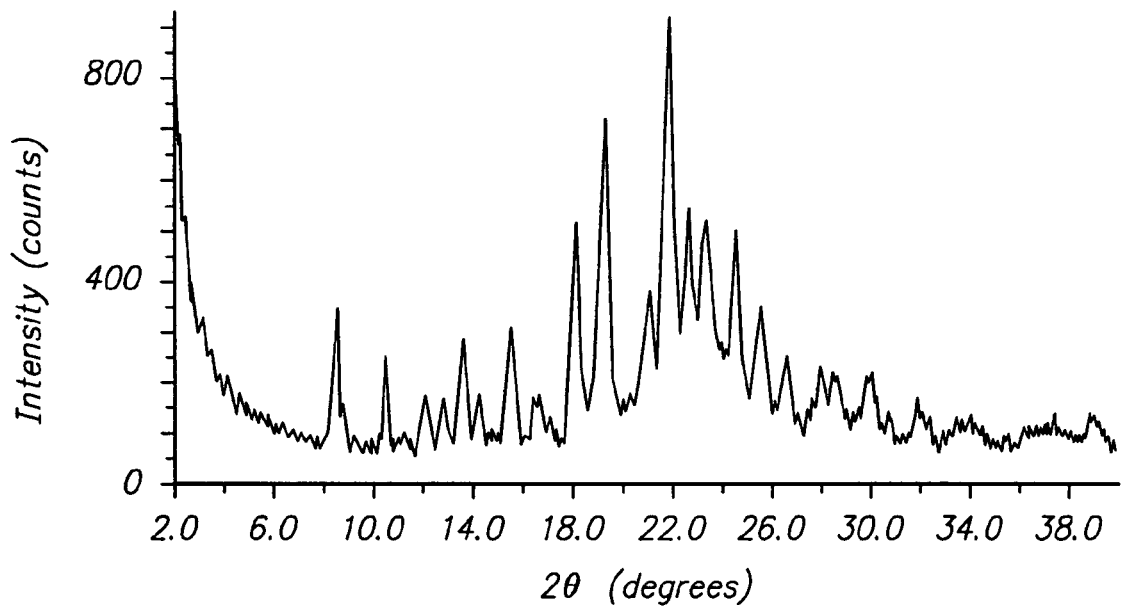
Figure 6:
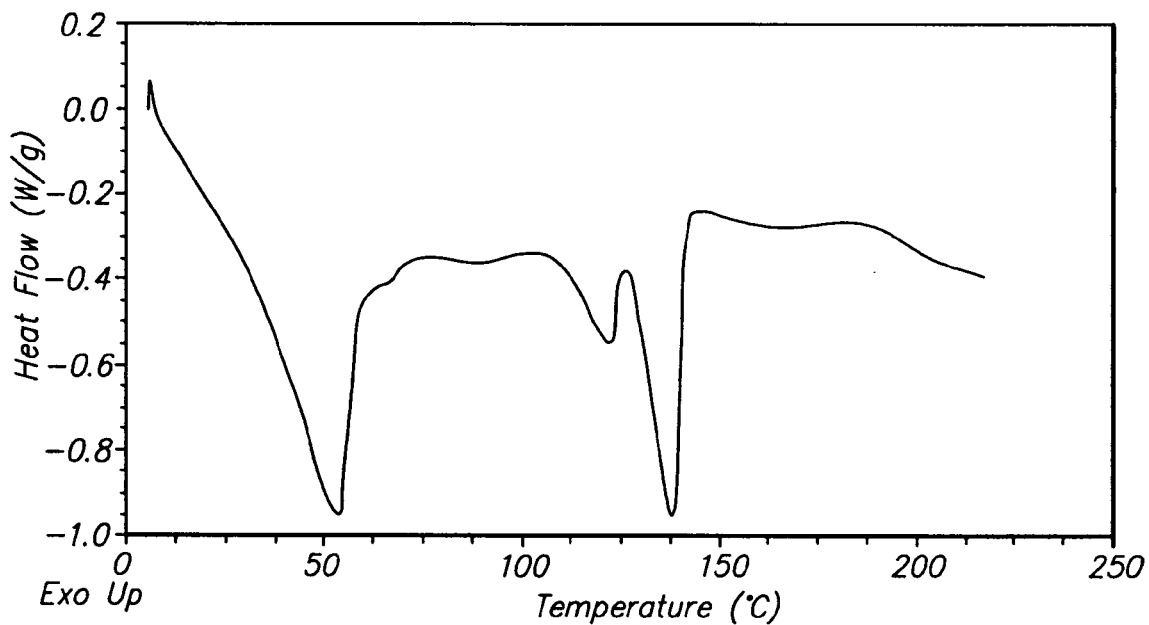
Figure 9:
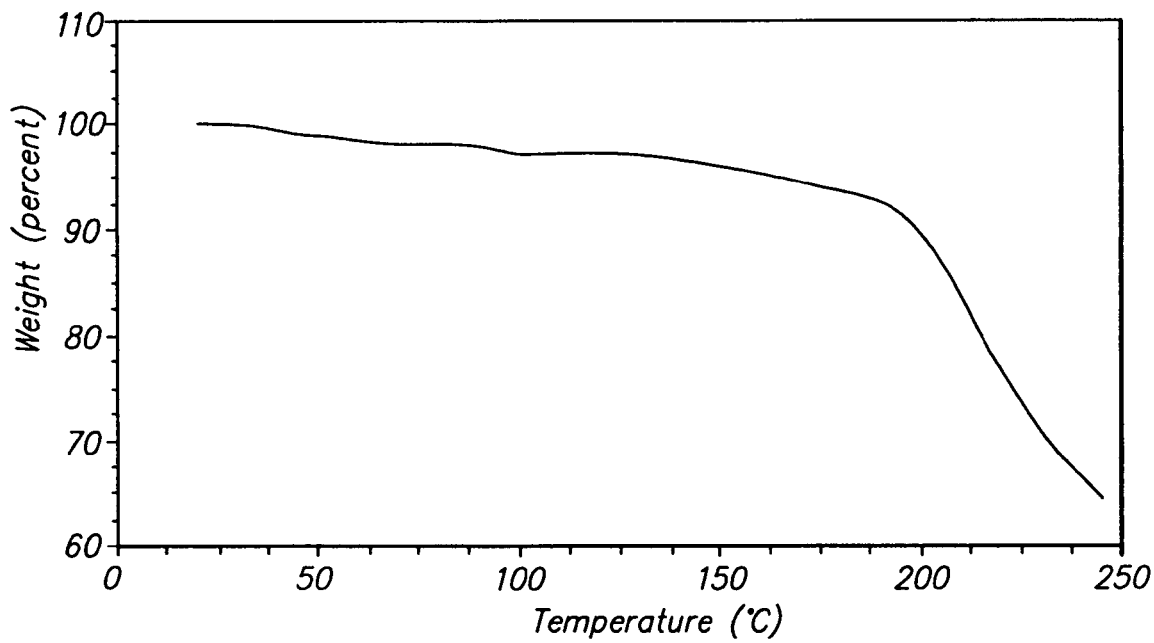

Preparation of Form III of Biphenyl-2-ylcarbamic acid 1-[2-(4-{[(R)-2-(3-Formylamino-4-hydroxyphenyl)-2-hydroxyethylamino]methyl}-2,5-dimethylphenylcarbamoyl)ethyl]piperidin-4-yl Ester A slurry of biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)-ethyl]piperidin-4-yl ester (54 mg) in ethanol (2 mL) was prepared and stirred at ambient temperature for 2 days. The solvent was removed by filtration, and the solids were dried at ambient temperature to provide Form III (48 mg). The PXRD, DSC and TGA spectra for this crystalline free base form are shown in FIGS. 3, 6 and 9, respectively.

Example 11

Preparation of Seed Crystals of Form II of Biphenyl-2-ylcarbamic acid 1-[2-(4-{[(R)-2-(3-Formylamino-4-hydroxyphenyl)-2-hydroxyethylamino]methyl}-2,5-dimethylphenylcarbamoyl)ethyl]piperidin-4-yl Ester Semi-crystalline biphenyl-2-ylcarbamic acid 1-[2-(4-{[(R)-2-(3-formylamino-4-hydroxyphenyl)-2-hydroxyethylamino]methyl}-2,5-dimethylphenyl-carbamoyl)ethyl]piperidin-4-yl ester (500 mg) was dissolved in methanol (50 mL) and water was added until the cloud point was reached. The resulting mixture was stirred at 25° C. for 3 hours and the resulting crystalline material was isolated by filtration to provide Form II of crystalline biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)-ethyl]piperidin-4-yl ester (420 mg).

Example 12

Crystallization of Form II of Biphenyl-2-ylcarbamic acid 1-[2-(4-{[(R)-2-(3-Formylamino-4-hydroxyphenyl)-2-hydroxyethylamino]methyl}-2,5-dimethylphenylcarbamoyl)ethyl]piperidin-4-yl Ester To a 3 L three-necked round-bottomed flask equipped with an over-head stirrer, temperature control and addition funnel was added semi-crystalline biphenyl-2-ylcarbamic acid 1-[2-(4-{[(R)-2-(3-formylamino-4-hydroxyphenyl)-2-hydroxyethylamino]methyl}-2,5-dimethylphenyl-carbamoyl)ethyl]piperidin-4-yl ester (14 g) and methanol (1.4 L). Water (500 mL) was added in one portion and then additional water (200 mL) was added slowly until the cloud point was reached. Seed crystals of Form II of biphenyl-2-ylcarbamic acid 1-[2-(4-{[(R)-2-(3-formylamino-4-hydroxyphenyl)-2-hydroxyethylamino]methyl}-2,5-dimethylphenyl-carbamoyl)ethyl]piperidin-4-yl ester (50 mg) were added and the resulting mixture was stirred at 25° C. for 3 hours at which time a free-flowing slurry had developed. Water (300 mL) was added over a 15-minute period and the resulting mixture was stirred at 25° C. overnight. The mixture was then filtered and the filter cake was washed with water (100 mL), air dried for about 2 hours and then dried under vacuum at room temperature for 48 hours to provide Form II of crystalline biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester (12.5 g, 99.6% purity).

Example 13

Powder X-Ray Diffraction

Powder x-ray diffraction patterns were obtained with a Thermo ARL X-Ray Diffractometer Model X'TRA (Thermo ARL SA, Switzerland) using Cu Kα radiation at 1.542 Å (45 kV, 40 mA) with a solid-state Peltier detector. The analysis was typically performed at a scan rate of 2°/min with a step size of 0.03° per point over a range of 2 to 40° in two-theta angle. Prior to measurement, a 30-second light hand grinding was performed on Form II to reduce the particle size. No mechanical particle size reduction was done on Form I and III. Samples were gently packed into a custom quartz-sample pan designed to fit into the instrument top-loading sample cup for analysis. The instrument was calibrated weekly to a silicon metal standard, within ±0.02° two-theta angle. Representative raw unprocessed PXRD patterns for Form I, Form II and Form III of crystalline biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)-ethyl]piperidin-4-yl ester are shown in FIGS. 1, 2 and 3, respectively.

Additionally, the following two-theta peak positions for each form were obtained using a profile fitting function including a background subtraction and smoothing routine:

Form I: 8.3±0.3; 10.7±0.3; 12.2±0.3; 13.5±0.3; 14.5±0.3; 15.2±0.3; 17.7±0.3; 18.2±0.3; 19.6±0.3; 20.7±0.3; 21.7±0.3 and 23.2±0.3.

Form II: 8.4±0.3; 10.4±0.3; 10.7±0.3; 11.9±0.3; 12.3±0.3; 12.6±0.3; 13.4±0.3; 13.6±0.3; 14.3±0.3; 14.7±0.3; 15.3±0.3; 16.8±0.3; 17.1±0.3; 17.8±0.3; 18.2±0.3; 18.7±0.3; 19.2±0.3; 19.8±0.3; 20.7±0.3; 21.6±0.3; 22.3±0.3; 22.5±0.3 and 23.2±0.3.

Form III: 8.5±0.3; 10.5±0.3; 11.3±0.3; 12.1±0.3; 12.8±0.3; 13.6±0.3; 14.2±0.3; 15.5±0.3; 16.6±0.3; 17.1±0.3; 18.1±0.3; 19.2±0.3; 21.0±0.3; 21.8±0.3; 22.6±0.3; 23.3±0.3 and 24.5±0.3.

Example 14

Differential Scanning Calorimetry

Differential scanning calorimetry (DSC) was performed using a TA Instruments Model Q-100 module with a Thermal Analyst controller. Data were collected and analyzed using TA Instruments Thermal Solutions software. A sample of about 1 mg was accurately weighed into an aluminum pan with lid. The sample was evaluated using a linear heating ramp of 5° C./min from ambient temperature to approximately 300° C. The DSC cell was purged with dry nitrogen during use. Representative DSC traces for samples of Form I, Form II and Form III of crystalline biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester are shown in FIGS. 4, 5 and 6, respectively. FIG. 5 demonstrate that Form II of crystalline biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester has excellent thermal stability with a melting point at about 143° C.

Example 15

Thermogravimetric Analysis

Thermogravimetric analysis (TGA) was performed using a TA Instruments Model Q-500 module equipped with high resolution capability. Data were collected and analyzed using TA Instruments Thermal Solutions software. A sample weighing about 10 mg was placed onto a platinum pan and scanned with a high resolution-heating rate from ambient temperature to 300° C. The balance and furnace chambers were purged with nitrogen flows during use. Representative TGA traces for samples of Form I, Form II and Form III of crystalline biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)-ethyl]piperidin-4-yl ester are shown in FIGS. 7, 8 and 9, respectively.

Example 16

Dynamic Moisture Sorption Assessment

Figure 10:
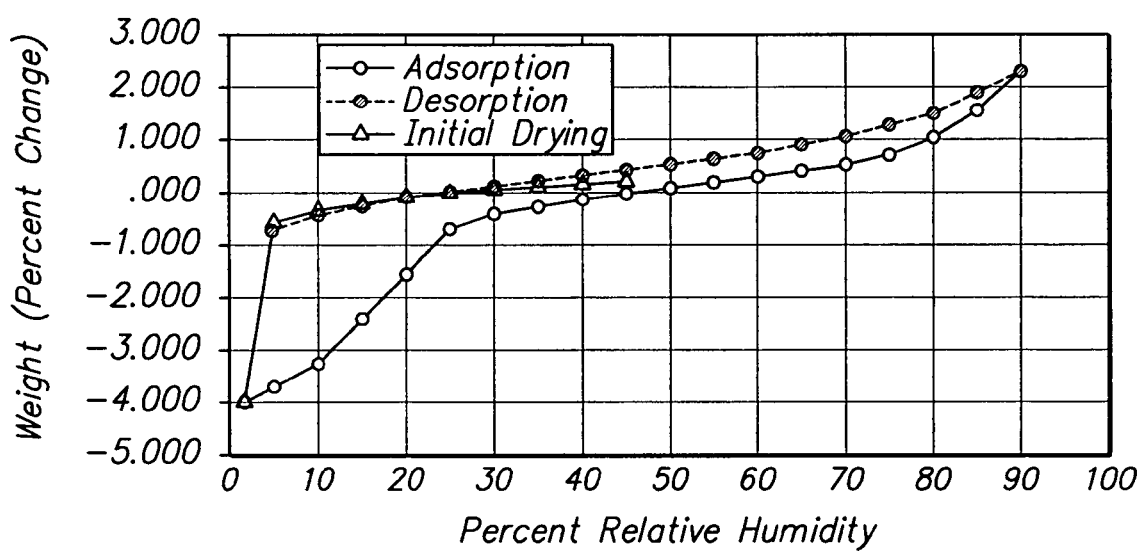
FIGS. 10, 11 and 12 show dynamic moisture sorption (DMS) traces for Forms I, II and III, respectively, of the crystalline free base of biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester.

A dynamic moisture sorption (DMS) assessment (also known as a moisture sorption-desorption profile) was performed for a hand ground samples of Form I, Form II and Form III of crystalline biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)-ethyl]piperidin-4-yl ester using a VTI atmospheric microbalance, SGA-100 system (VTI Corp., Hialeah, Fla. 33016). A sample size of approximately 10 mg was used and the humidity was set at the ambient value at the start of the analysis. A typical DMS analysis consisted of three scans: ambient to 2% relative humidity (RH), 2% RH to 90% RH, 90% RH to 5% RH at a scan rate of 5% RH/step. The mass was measured every two minutes and the RH was changed to the next value (±5% RH) when the mass of the sample was stable to within 0.01% for 5 consecutive points. Representative DMS traces for Form I, Form II and Form III are shown in FIGS. 10, 11 and 12, respectively.

Figure 11:
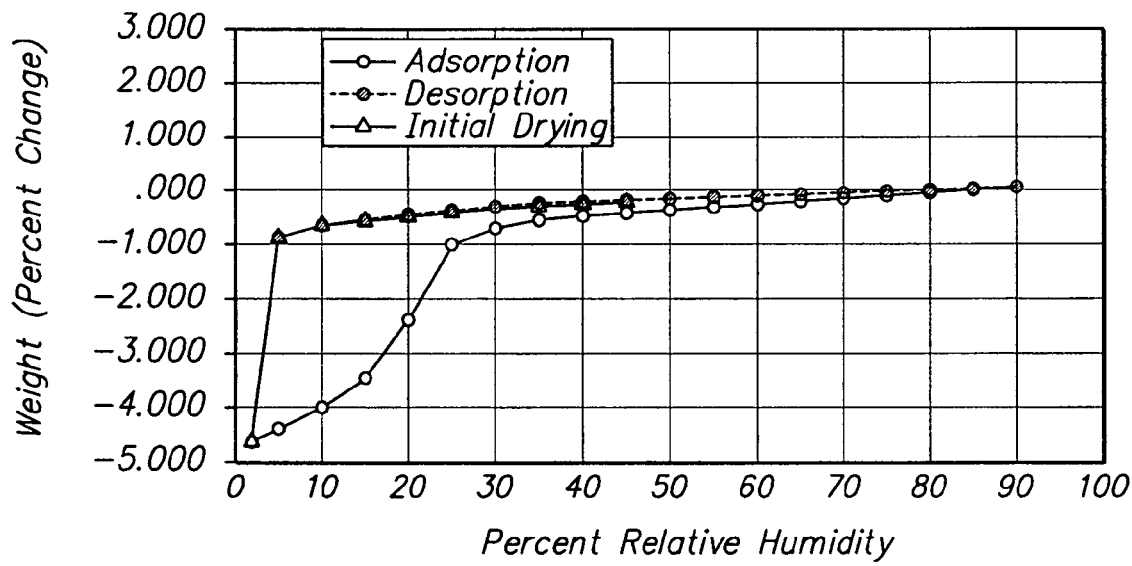
Figure 12:
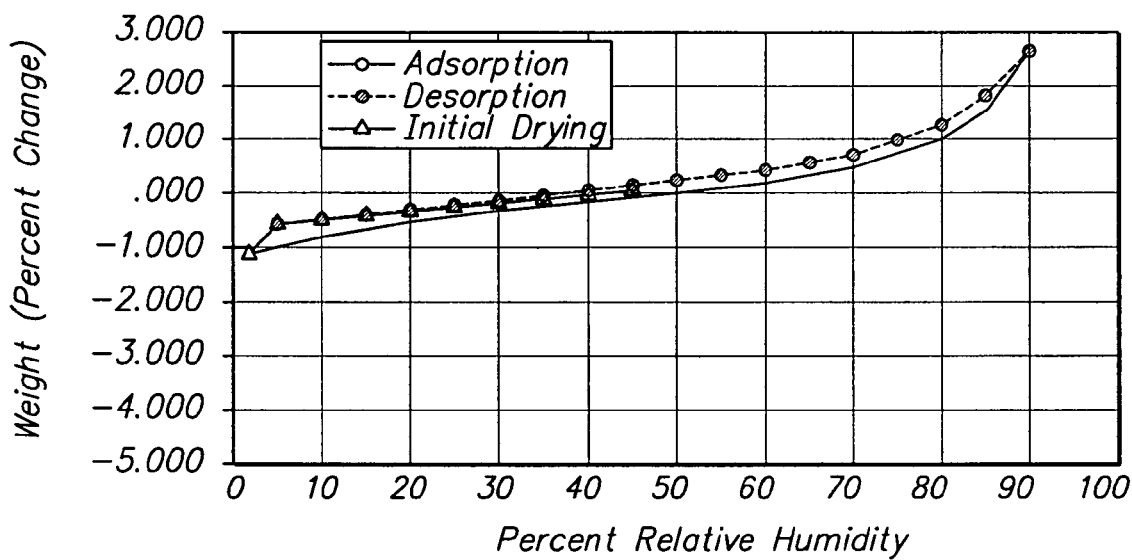

The DMS trace of FIG. 11 demonstrates that Form II had a reversible sorption/desorption profile with moderate (<5%) hygroscopicity. Form II had an insignificant weight gain of about 0.3 weight % in the humidity range of 40% RH to 75% RH. The reversible moisture sorption/desorption profile demonstrates that Form II possesses an acceptable hygroscopicity and is not deliquescent.

Example 17

Cell Culture and Membrane Preparation From Cells Expressing Human $M_1$, $M_2$, $M_3$ and $M_4$ Muscarinic Receptors CHO cell lines stably expressing cloned human $hM_1$, $hM_2$, $hM_3$ and $hM_4$ muscarinic receptor subtypes, respectively, were grown to near confluency in Hams F-12 media supplemented with 10% FBS and 250 µg/mL Geneticin. The cells were grown in a 5% $CO_2$, 37° C. incubator and lifted with 2 mM EDTA in dPBS. Cells were collected by 5 minute centrifugation at 650×g, and cell pellets were either stored frozen at −80° C. or membranes were prepared immediately for use. For membrane preparation, cell pellets were resuspended in lysis buffer and homogenized with a Polytron PT-2100 tissue disrupter (Kinematica AG; 20 seconds×2 bursts). Crude membranes were centrifuged at 40,000×g for 15 minutes at 4° C. The membrane pellet was then resuspended with re-suspension buffer and homogenized again with the Polytron tissue disrupter. The protein concentration of the membrane suspension was determined by the method described in Lowry et al., 1951, *Journal of Biochemistry*, 193, 265. All membranes were stored frozen in aliquots at −80° C. or used immediately. Aliquots of prepared $hM_5$ receptor membranes were purchased directly from PerkinElmer, Inc. (Wellesley, Mass.) and stored at −80° C. until use.

Example 18

Radioligand Binding Assay for Muscarinic Receptors

Radioligand binding assays for cloned muscarinic receptors were performed in 96-well microtiter plates in a total assay volume of 100 µL. CHO cell membranes stably expressing either the $hM_1$, $hM_2$, $hM_3$, $hM_4$ or $hM_5$ muscarinic subtype were diluted in assay buffer to the following specific target protein concentrations (µg/well): 10 µg for $hM_1$, 10-15 µg for $hM_2$, 10-20 µg for $hM_3$, 10-20 µg for $hM_4$, and 10-12 µg for $hM_5$ to get similar signals (cpm). The membranes were briefly homogenized using a Polytron tissue disrupter (10 seconds) prior to assay plate addition. Saturation binding studies for determining $K_D$ values of the radioligand were performed using L-[N-methyl-$^3$H]scopolamine methyl chloride ([$^3$H]-NMS) (TRK666, 84.0 Ci/mmol, Amersham Pharmacia Biotech, Buckinghamshire, England) at concentrations ranging from 0.001 nM to 20 nM. Displacement assays for determination of $K_i$ values of test compounds were performed with [$^3$H]-NMS at 1 nM and eleven different test compound concentrations. The test compounds were initially dissolved to a concentration of 400 µM in dilution buffer and then serially diluted 5× with dilution buffer to final concentrations ranging from 10 pM to 100 µM. The addition order and volumes to the assay plates were as follows: 25 µL radioligand, 25 µL diluted test compound, and 50 µL membranes. Assay plates were incubated for 60 minutes at 37° C. Binding reactions were terminated by rapid filtration over GF/B glass fiber filter plates (PerkinElmer, Inc.) pre-treated in 1% BSA. Filter plates were rinsed three times with wash buffer (10 mM HEPES) to remove unbound radioactivity. The plates were then air-dried and 50 µL Microscint-20 liquid scintillation fluid (PerkinElmer, Inc.) were added to each well. The plates were then counted in a PerkinElmer Topcount liquid scintillation counter (PerkinElmer, Inc.). Binding data were analyzed by nonlinear regression analysis with the GraphPad Prism Software package (GraphPad Software, Inc., San Diego, Calif.) using the one-site competition model. $K_i$ values for test compounds were calculated from observed $IC_{50}$ values and the $K_D$ value of the radioligand using the Cheng-Prusoff equation (Cheng Y; Prusoff W H. (1973) *Biochemical Pharmacology*, 22(23):3099-108). $K_i$ values were converted to $pK_i$ values to determine the geometric mean and 95% confidence intervals. These summary statistics were then converted back to $K_i$ values for data reporting.

In this assay, a lower $K_i$ value indicates that the test compound has a higher binding affinity for the receptor tested. Biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester (compound of formula I) was found to have a $K_i$ value of less than 10 nM for the $M_1$, $M_2$, $M_3$, $M_4$ and $M_5$ muscarinic receptor subtypes.

Example 19

Cell Culture and Membrane Preparation From Cells Expressing Human $\beta_1$, $\beta_2$ or $\beta_3$ Adrenergic Receptors Human embryonic kidney (HEK-293) cell lines stably expressing cloned human $\beta_1$ and $\beta_2$ adrenergic receptors or Chinese hamster ovarian (CHO) cell lines stably expressing cloned human $\beta_3$ adrenergic receptors were grown to near confluency in DMEM or Hams F-12 media with 10% FBS in the presence of 500 µg/mL Geneticin. The cell monolayer was lifted with 2 mM EDTA in PBS. Cells were pelleted by centrifugation at 1,000 rpm, and cell pellets were either stored frozen at −80° C. or membranes were prepared immediately for use. For preparation of $\beta_1$ and $\beta_2$ receptor expressing membranes, cell pellets were re-suspended in lysis buffer (10 mM HEPES/HCl, 10 mM EDTA, pH 7.4 at 4° C.) and homogenized using a tight-fitting Dounce glass homogenizer (30 strokes) on ice. For the more protease-sensitive $\beta_3$ receptor expressing membranes, cell pellets were homogenated in lysis buffer (10 mM Tris/HCl, pH 7.4) supplemented with one tablet of "Complete Protease Inhibitor Cocktail Tablets with 2 mM EDTA" per 50 mL buffer (Roche Molecular Biochemicals, Indianapolis, Ind.). The homogenate was centrifuged at 20,000×g, and the resulting pellet was washed once with lysis buffer by re-suspension and centrifugation as above. The final pellet was then re-suspended in ice-cold binding assay buffer (75 mM Tris/HCl pH 7.4, 12.5 mM $MgCl_2$, 1 mM EDTA). The protein concentration of the membrane suspension was determined by the methods described in Lowry et al., 1951, *Journal of Biological Chemistry*, 193, 265; and Bradford, *Analytical Biochemistry*, 1976, 72, 248-54. All membranes were stored frozen in aliquots at −80° C. or used immediately.

Example 20

Radioligand Binding Assay for Human $\beta_1$, $\beta_2$ and $\beta_3$ Adrenergic Receptors Binding assays were performed in 96-well microtiter plates in a total assay volume of 100 µL with 10-15 µg of membrane protein containing the human $\beta_1$, $\beta_2$ or $\beta_3$ adrenergic receptors in assay buffer (75 mM Tris/HCl pH 7.4 at 25° C., 12.5 mM $MgCl_2$, 1 mM EDTA, 0.2% BSA). Saturation binding studies for determining $K_d$ values of the radioligand were done using [$^3$H]-dihydroalprenolol (NET-720, 100 Ci/mmol, PerkinElmer Life Sciences Inc., Boston, Mass.) for the $\beta_1$ and $\beta_2$ receptors and [$^{125}$I]-(−)-iodocyanopindolol (NEX-189, 220 Ci/mmol, PerkinElmer Life Sciences Inc., Boston, Mass.) at 10 or 11 different concentrations ranging from 0.01 nM to 20 nM. Displacement assays for determination of $K_i$ values of test compounds were done with [$^3$H]-dihydroalprenolol at 1 nM and [$^{125}$I]-(−)-iodocyanopindolol at 0.5 nM for 10 or 11 different concentrations of test compound ranging from 10 pM to 10 µM. Non-specific binding was determined in the presence of 10 µM propranolol. Assays were incubated for 1 hour at 37° C., and then binding reactions were terminated by rapid filtration over GF/B for the $\beta_1$ and $\beta_2$ receptors or GF/C glass fiber filter plates for the $\beta_3$ receptors (Packard BioScience Co., Meriden, Conn.) pre-soaked in 0.3% polyethyleneimine. Filter plates were washed three times with filtration buffer (75 mM Tris/HCl pH 7.4 at 4° C., 12.5 mM $MgCl_2$, 1 mM EDTA) to remove unbound radioactivity. The plates were then dried and 50 µL of Microscint-20 liquid scintillation fluid (Packard BioScience Co., Meriden, Conn.) was added and plates were counted in a Packard Topcount liquid scintillation counter (Packard BioScience Co., Meriden, Conn.). Binding data were analyzed by nonlinear regression analysis with the GraphPad Prism Software package (GraphPad Software, Inc., San Diego, Calif.) using the 3-parameter model for one-site competition. The curve minimum was fixed to the value for nonspecific binding, as determined in the presence of 10 µM propranolol. $K_i$ values for test compounds were calculated from observed $IC_{50}$ values and the $K_d$ value of the radioligand using the Cheng-Prusoff equation (Cheng Y, and Prusoff W H., *Biochemical Pharmacology*, 1973, 22, 23, 3099-108).

In this assay, a lower $K_i$ value indicates that a test compound has a higher binding affinity for the receptor tested. Biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester (compound of formula I) was found to have a $K_i$ value of less than 10 nM for the $\beta_2$ adrenergic receptor and $K_i$ values greater than 1000 nM for the $\beta_1$ and $\beta_3$ adrenergic receptors.

Example 21

Functional Assays of Antagonism for Muscarinic Receptor Subtypes

Assay A—Blockade of Agonist-Mediated Inhibition of cAMP Accumulation

In this assay, the functional potency of a test compound as an antagonist for the $hM_2$ receptor was determined by measuring the ability of the test compound to block oxotremorine-inhibition of forskolin-mediated cAMP accumulation in CHO-K1 cells expressing the $hM_2$ receptor. cAMP assays were performed in a radioimmunoassay format using the Flashplate Adenylyl Cyclase Activation Assay System with $^{125}$I-cAMP (NEN SMP004B, PerkinElmer Life Sciences Inc., Boston, Mass.), according to the manufacturer's instructions. Cells were rinsed once with dPBS and lifted with Trypsin-EDTA solution (0.05% trypsin/0.53 mM EDTA) as described in the Cell Culture and Membrane Preparation section above. The detached cells were washed twice by centrifugation at 650×g for five minutes in 50 mL dPBS. The cell pellet was then re-suspended in 10 mL dPBS, and the cells were counted with a Coulter Z1 Dual Particle Counter (Beckman Coulter, Fullerton, Calif.). The cells were centrifuged again at 650×g for five minutes and re-suspended in stimulation buffer to an assay concentration of $1.6 \times 10^6$ to $2.8 \times 10^6$ cells/mL.

The test compound was initially dissolved to a concentration of 400 µM in dilution buffer (dPBS supplemented with 1 mg/mL BSA (0.1%)), and then serially diluted with dilution buffer to final molar concentrations ranging from 100 µM to 0.1 nM. Oxotremorine was diluted in a similar manner.

To measure oxotremorine inhibition of adenylyl cyclase activity, 25 µL forskolin (25 µM final concentration diluted in dPBS), 25 µL diluted oxotremorine, and 50 µL cells were added to agonist assay wells. To measure the ability of a test compound to block oxotremorine-inhibited adenylyl cyclase activity, 25 µL forskolin and oxotremorine (25 µM and 5 µM final concentrations, respectively, diluted in dPBS), 25 µL diluted test compound, and 50 µL cells were added to remaining assay wells.

Reactions were incubated for 10 minutes at 37° C. and stopped by addition of 100 µL ice-cold detection buffer. Plates were sealed, incubated overnight at room temperature and counted the next morning on a PerkinElmer TopCount liquid scintillation counter (PerkinElmer Inc., Wellesley, Mass.). The amount of cAMP produced (pmol/well) was calculated based on the counts observed for the samples and cAMP standards, as described in the manufacturer's user manual. Data was analyzed by nonlinear regression analysis with the GraphPad Prism Software package (GraphPad Software, Inc., San Diego, Calif.) using the non-linear regression, one-site competition equation. The Cheng-Prusoff equation was used to calculate the $K_{obs}$, using the $EC_{50}$ of the oxotremorine concentration-response curve and the oxotremorine assay concentration as the $K_D$ and [L], respectively.

In this assay, a lower $k_{obs}$ value indicates that the test compound has a higher functional activity at the receptor tested. Biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester (compound of formula I) was found to have a $K_{obs}$ value of less than about 10 nM for blockade of oxotremorine-inhibition of forskolin-mediated cAMP accumulation in CHO-K1 cells expressing the $hM_2$ receptor.

Assay B—Blockade of Agonist-Mediated [$^{35}$S]GTPγS Binding

In this functional assay, the functional potency of a test compound as an antagonist of the $hM_2$ receptor was determined by measuring the ability of the test compound to block oxotremorine-stimulated [$^{35}$S]GTPγS binding in CHO-K1 cells expressing the $hM_2$ receptor.

At the time of use, frozen membranes were thawed and then diluted in assay buffer with a final target tissue concentration of 5 to 10 μg protein per well. The membranes were briefly homogenized using a Polytron PT-2100 tissue disrupter and then added to the assay plates.

The $EC_{90}$ value (effective concentration for 90% maximal response) for stimulation of [$^{35}$S]GTPγS binding by the agonist oxotremorine was determined in each experiment.

To determine the ability of a test compound to inhibit oxotremorine-stimulated [$^{35}$S]GTPγS binding, the following was added to each well of 96 well plates: 25 μL of assay buffer with [$^{35}$S]GTPγS (0.4 nM), 25 μL of oxotremorine($EC_{90}$) and GDP (3 uM), 25 μL of diluted test compound and 25 μL CHO cell membranes expressing the $hM_2$ receptor. The assay plates were then incubated at 37° C. for 60 minutes. The assay plates were filtered over 1% BSA-pretreated GF/B filters using a PerkinElmer 96-well harvester. The plates were rinsed with ice-cold wash buffer for 3×3 seconds and then air or vacuum dried. Microscint-20 scintillation liquid (50 μL) was added to each well, and each plate was sealed and radioactivity counted on a Topcounter (PerkinElmer). Data were analyzed by nonlinear regression analysis with the GraphPad Prism Software package (GraphPad Software, Inc., San Diego, Calif.) using the non-linear regression, one-site competition equation. The Cheng-Prusoff equation was used to calculate the $K_{obs}$, using the $IC_{50}$ values of the concentration-response curve for the test compound and the oxotremorine concentration in the assay as the $K_D$ and [L], ligand concentration, respectively.

In this assay, a lower $K_{obs}$ value indicates that the test compound has a higher functional activity at the receptor tested. Biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester (compound of formula I) was found to have a $K_{obs}$ value of less than about 10 nM for blockade of oxotremorine-stimulated [$^{35}$S]GTPγS binding in CHO-K1 cells expressing the $hM_2$ receptor.

Assay C—Blockade of Agonist-Mediated Calcium Release via FLIPR Assays

In this functional assay, the functional potency of a test compound as an antagonist of $hM_1$, $hM_3$ and $cM_5$ receptors was determined by measuring the ability of the test compound to inhibit agonist-mediated increases in intracellular calcium.

CHO cells stably expressing the receptors were seeded into 96-well FLIPR plates the night before the assay was done. Seeded cells were washed twice with FLIPR buffer (10 mM HEPES, pH 7.4, 2 mM calcium chloride, 2.5 mM probenecid in Hank's Buffered Salt Solution (HBSS) without calcium and magnesium) using Cellwash (MTX Labsystems, Inc.) to remove growth media. After washing, each well contained 50 μL of FLIPR buffer. The cells were then incubated with 50 μL/well of 4 μM FLUO-4AM (a 2× solution was made) for 40 minutes at 37° C., 5% carbon dioxide. Following the dye incubation period, cells were washed two times with FLIPR buffer, leaving a final volume of 50 μL in each well.

The dose-dependent stimulation of intracellular $Ca^{2+}$ release for oxotremorine was determined so that the test compound could be measured against oxotremorine stimulation at an $EC_{90}$ concentration. Cells were first incubated with compound dilution buffer for 20 minutes and then oxotremorine was added. An $EC_{90}$ value for oxotremorine was generated according to the method detailed in the FLIPR measurement and data reduction section below, in conjunction with the formula $EC_F = ((F/100-F)^{\wedge}1/H)*EC_{50}$. An oxotremorine concentration of $3\times EC_F$ was prepared in stimulation plates such that an $EC_{90}$ concentration of oxotremorine was added to each well in test assay plates.

The parameters used for the FLIPR were: exposure length of 0.4 seconds, laser strength of 0.5 watts, excitation wavelength of 488 nm, and emission wavelength of 550 nm. Baseline was determined by measuring the change in fluorescence for 10 seconds prior to addition of oxotremorine. Following oxotremorine stimulation, the FLIPR continuously measured the change of fluorescence every 0.5 to 1 second for 1.5 minutes to capture the maximum fluorescence change.

The change of fluorescence was expressed as maximum fluorescence minus baseline fluorescence for each well. The raw data was analyzed against the logarithm of test compound concentration by nonlinear regression with GraphPad Prism (GraphPad Software, Inc., San Diego, Calif.) using the built-in model for sigmoidal dose-response. Antagonist $K_{obs}$ values were determined by Prism using the oxotremorine $EC_{50}$ value as the $K_D$ and the oxotremorine $EC_{90}$ for the ligand concentration according to the Cheng-Prusoff equation (Cheng & Prusoff, 1973).

In this assay, a lower $K_{obs}$ value indicates that the test compound has a higher functional activity at the receptor tested. Biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester (compound of formula I) was found to have a $K_{obs}$ value of less than about 10 nM for blockade of agonist-mediated calcium release in CHO cells stably expressing the $hM_1$, $hM_3$ and $cM_5$ receptors.

Example 22

Whole-cell cAMP Flashplate Assay in HEK-293 and CHO Cell Lines Heterologously Expressing Human $β_1$, $β_2$ or $β_3$ Adrenergic Receptors cAMP assays were performed in a radioimmunoassay format using the Flashplate Adenylyl Cyclase Activation Assay System with [$^{125}$I]-cAMP (NEN SMP004, PerkinElmer Life Sciences Inc., Boston, Mass.), according to the manufacturers instructions. For the determination of $\beta_1$ and $\beta_2$ receptor agonist potency ($EC_{50}$), receptor agonist potency ($EC_{50}$), CHO-K1 HEK-293 cell lines stably expressing cloned human, $\beta_1$ and $\beta_2$ receptors were grown to near confluency in DMEM supplemented with 10% FBS and Geneticin (500 µg/mL). For the determination $\beta_3$ receptor agonist potency ($EC_{50}$), CHO-K1 cell line stably expressing cloned human or $\beta_3$ adrenergic receptors was grown to near confluency in Hams F-12 media supplemented with 10% FBS and Geneticin (250 µg/mL). Cells were rinsed with PBS and detached in dPBS (Dulbecco's Phosphate Buffered Saline, without $CaCl_2$ and $MgCl_2$) containing 2 mM EDTA or Trypsin-EDTA solution (0.05% trypsin/0.53 mM EDTA). After counting cells in Coulter cell counter, cells were pelleted by centrifugation at 1,000 rpm and re-suspended in stimulation buffer containing IBMX (PerkinElmer Kit) pre-warmed to room temperature to a concentration of $1.6 \times 10^6$ to $2.8 \times 10^6$ cells/mL. About 40,000 to 80,000 cells per well were used in this assay. Test compounds (10 mM in DMSO) were diluted into PBS containing 0.1% BSA in Beckman Biomek-2000 and tested at 11 different concentrations ranging from 100 µM to 1 pM. Reactions were incubated for 10 min at 37° C. and stopped by adding 100 µL of cold detection buffer containing [$^{125}$I]-cAMP (NEN SMP004, PerkinElmer Life Sciences, Boston, Mass.). The amount of cAMP produced (pmol/well) was calculated based on the counts observed for the samples and cAMP standards as described in the manufacturer's user manual. Data were analyzed by nonlinear regression analysis with the GraphPad Prism Software package (GraphPad Software, Inc., San Diego, Calif.) with the sigmoidal equation. The Cheng-Prusoff equation (Cheng Y, and Prusoff W H., *Biochemical Pharmacology*, 1973, 22, 23, 3099-108) was used to calculate the $EC_{50}$ values.

In this assay, a lower $EC_{50}$ value indicates that the test compound has a higher functional activity at the receptor tested. Biphenyl-2-ylcarbamic acid 1-[2-(4-{[(R)-2-(3-formylamino-4-hydroxyphenyl)-2-hydroxyethylamino]methyl}-2,5-dimethylphenyl-carbamoyl)ethyl]piperidin-4-yl ester (compound of formula I) was found to have an $EC_{50}$ value less than about 10 nM for the $\beta_2$ adrenergic receptor; an $EC_{50}$ value of about 30 nM for the $\beta_1$ adrenergic receptor; and an $EC_{50}$ value greater than 700 nM for the $\beta_3$ adrenergic receptor.

Example 23

Whole-cell cAMP Flashplate Assay With a Lung Epithelial Cell Line Endogenously Expressing Human $\beta_2$ Adrenergic Receptor In this assay, the agonist potency and intrinsic activity of a test compound were determined using a cell line expressing endogenous levels of the $\beta_2$ adrenergic receptor. Cells from a human lung epithelial cell line (BEAS-2B) (ATCC CRL-9609, American Type Culture Collection, Manassas, Va.) (January B, et al., *British Journal of Pharmacology*, 1998, 123, 4, 701-11) were grown to 75-90% confluency in complete, serum-free medium (LHC-9 medium containing epinephrine and retinoic acid, Biosource International, Camarillo, Calif.). The day before the assay, the medium was switched to LHC-8 (no epinephrine or retinoic acid, Biosource International, Camarillo, Calif.). cAMP assays were performed in a radioimmunoassay format using the Flashplate Adenylyl Cyclase Activation Assay System with [$^{125}$I]-cAMP (NEN SMP004, PerkinElmer Life Sciences Inc., Boston, Mass.), according to the manufacturers instructions.

On the day of the assay, cells were rinsed with PBS, lifted by scraping with 5 mM EDTA in PBS, and counted. Cells were pelleted by centrifugation at 1,000 rpm and re-suspended in stimulation buffer pre-warmed to 37° C. at a final concentration of 600,000 cells/mL. Cells were used at a final concentration of 100,000 to 120,000 cells/well in this assay. Test compounds were serially diluted into assay buffer (75 mM Tris/HCl pH 7.4 at 25° C., 12.5 mM $MgCl_2$, 1 mM EDTA, 0.2% BSA) in Beckman Biomek-2000. Test compounds were tested in the assay at 11 different concentrations, ranging from 10 µM to 10 pM. Reactions were incubated for 10 min at 37° C. and stopped by addition of 100 µL of ice-cold detection buffer. Plates were sealed, incubated over night at 4° C. and counted the next morning in a Topcount scintillation counter (Packard BioScience Co., Meriden, Conn.). The amount of cAMP produced per mL of reaction was calculated based on the counts observed for samples and cAMP standards, as described in the manufacturer's user manual. Data were analyzed by nonlinear regression analysis with the GraphPad Prism Software package (GraphPad Software, Inc., San Diego, Calif.) using the 4-parameter model for sigmoidal dose-response.

In this assay, a lower $EC_{50}$ value indicates that the test compound has a higher functional activity at the receptor tested. Biphenyl-2-ylcarbamic acid 1-[2-(4-{[(R)-2-(3-formylamino-4-hydroxyphenyl)-2-hydroxyethylamino]methyl}-2,5-dimethylphenyl-carbamoyl)ethyl]piperidin-4-yl ester (compound of formula I) was found to have an $EC_{50}$ value of less than 10 nM with intrinsic activity value of greater than 0.3 compared with a full $\beta_2$ agonist isoproterenol (1.0).

Example 24

Einthoven Assay for Determining Bronchoprotective Efficacy and Duration

In this assay, the bronchoprotective efficacy and duration of test compounds were determined using guinea pigs. This assay was derived from the procedures described in Einthoven (1892) *Pfugers Arch.* 51: 367-445; and Mohammed et al. (2000) *Pulm Pharmacol Ther.* 13(6):287-92. In this assay, changes in ventilation pressure serve as a surrogate measure of airway resistance. Following pre-treatment with a test compound, muscarinic antagonist potency was determined using bronchoconstrictor dose-response curves to intravenous methacholine in the presence of propranolol. Similarly, $\beta_2$ agonist bronchoprotective potency was determined using histamine. Combined bronchoprotective potency was determined using methacholine in the absence of propranolol.

The assay was conducted using male Duncan-Hartley guinea pigs (Harlan, Indianapolis, Ind.), weighing between 250 and 400 g. A test compound or vehicle (i.e., sterile water) was dosed by inhalation (IH) over a 10 minute time period in a whole body exposure dosing chamber (R+S Molds, San Carlos, Calif.) using 5 mL of dosing solution. Animals were exposed to an aerosol generated from an LC Star Nebulizer Set (Model 22F51, PARI Respiratory Equipment, Inc. Midlothian, Va.) driven by Bioblend (a mixture of 5% $CO_2$; 21% $O_2$; and 74% $N_2$) at a pressure of 22 psi. Pulmonary function was evaluated at various time points after inhalation dosing.

Seventy-five minutes prior to the start of the assay, the guinea pigs were anesthetized with an intramuscular (IM) injection of a mixture of ketamine (43.7 mg/kg/xylazine (3.5 mg/kg)/acepromazine (1.05 mg/kg). A supplemental dose of this mixture (50% of initial dose) was administered as needed. The jugular vein and carotid artery were isolated and cannulated with saline-filled polyethylene catheters (microrenathane and PE-50, respectively, Beckton Dickinson, Sparks, Md.). The carotid artery was connected to a pressure transducer to allow the measurement of blood pressure and the jugular vein cannula was used for IV injection of either methacholine or histamine. The trachea was then dissected free and cannulated with a 14G needle (#NE-014, Small Parts, Miami Lakes, Fla.). Once the cannulations were complete, the guinea pigs were ventilated using a respirator (Model 683, Harvard Apparatus, Inc., Mass.) set at a stroke volume of 1 mL/100 g body weight but not exceeding 2.5 mL volume, and at a rate of 100 strokes per minute. Ventilation pressure (VP) was measured in the tracheal cannula using a Biopac transducer connected to a Biopac (TSD 137C) pre-amplifier. Body temperature was maintained at 37° C. using a heating pad. Prior to initiating data collection, pentobarbital (25 mg/kg) was administered intraperitoneally (IP) to suppress spontaneous breathing and obtain a stable baseline. The changes in VP were recorded on a Biopac Windows data collection interface. Baseline values were collected for at least 5 minutes, after which time guinea pigs were challenged IV non-cumulatively with 2-fold incremental doses of the bronchoconstrictor (methacholine or histamine). When methacholine was used as the bronchoconstrictor agent, animals were pre-treated with propranolol (5 mg/kg, IV) to isolate the antimuscarinic effects of the test compound. The propranolol was administered 30 minutes prior to construction of the dose-response curve to methacholine or histamine. Changes in VP were recorded using the Acknowledge Data Collection Software (Santa Barbara, Calif.). After the completion of study, the animals were euthanized.

Change in VP was measured in cm of water. Change in VP (cm H$_2$O)=peak pressure (after bronchoconstrictor challenge)−peak baseline pressure. The dose-response curve to methacholine or histamine was fitted to a four parameter logistic equation using GraphPad Prism, version 3.00 for Windows (GraphPad Software, San Diego, Calif.). The following equation was used:

$$Y=\text{Min}+(\text{Max}-\text{Min})/(1+10^{((\log ID50-X)\cdot Hillslope)})$$

where X is the logarithm of dose, Y is the response. Y starts at Min and approaches asymptotically to Max with a sigmoidal shape.

The percent inhibition of the bronchoconstrictor response to a submaximal dose of methacholine or histamine was calculated at each dose of the test compound using the following equation: % Inhibition of response=100−((peak pressure (after bronchoconstrictor challenge, treated)−peak baseline pressure (treated)/(peak pressure (after bronchoconstrictor challenge, water)−peak baseline pressure (water)×100). Inhibition curves were fitted using the four parameter logistic equation from GraphPad software. ID$_{50}$ (dose required to produce 50% inhibition of the bronchoconstrictor response) and Emax (maximal inhibition) were also estimated wherever appropriate.

The magnitude of bronchoprotection at different timepoints after inhalation of the test compound was used to estimate the pharmacodynamic half-life (PD T$_{1/2}$). PD T$_{1/2}$ was determined using a non-linear regression fit using a one-phase exponential decay equation (GraphPad Prism, Version 4.00): Y=Span*exp(−K*X)+Plateau; Starts at Span+Plateau and decays to Plateau with a rate constant K. The PD T$_{1/2}$=0.69/K. Plateau was constrained to 0.

At 1.5 hours post-dose, biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester (compound of formula I) was found to have an ID$_{50}$ of less than about 50 μg/mL for both methacholine-induced bronchoconstriction and histamine-induced bronchoconstriction.

Additionally, this compound produced significant bronchoprotection for up to about 72 hours when administered as a single sub-maximal dose (100 μg/mL). In this assay, salmeterol (3 μg/mL, IH) (a β$_2$ adrenergic receptor agonist) exhibited significant bronchoprotection for 6 to 14 hours; and tiotropium (10 μg/mL) (a muscarinic receptor antagonist) exhibited significant bronchoprotection for greater than 72 hours.

While the present invention has been described with reference to specific aspects or embodiments thereof, it will be understood by those of ordinary skill in the art that various changes can be made or equivalents can be substituted without departing from the true spirit and scope of the invention. Additionally, to the extent permitted by applicable patent statutes and regulations, all publications, patents and patent applications cited herein are hereby incorporated by reference in their entirety to the same extent as if each document had been individually incorporated by reference herein.

What is claimed is:

1. Form I of a crystalline free base of biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester characterized by a powder x-ray diffraction pattern having diffraction peaks at 2θ values of about 17.7±0.3, 18.2±0.3, 21.7±0.3 and 23.2±0.3.

2. Form II of a crystalline free base of biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester characterized by a powder x-ray diffraction pattern having diffraction peaks at 2θ values of about 20.7±0.3, 21.6±0.3, 22.5±0.3 and 23.2±0.3.

3. Form III of a crystalline free base of biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester characterized by a powder x-ray diffraction pattern having diffraction peaks at 2θ values of about 15.5±0.3, 18.1±0.3, 19.2±0.3 and 21.8±0.3.

4. The crystalline free base form of claim 1, wherein the crystalline free base form is characterized by a powder x-ray diffraction pattern in which the peak positions are substantially in accordance with the peak positions of the pattern shown in FIG. 1.

5. The crystalline free base form of claim 2, wherein the crystalline free base form is characterized by a powder x-ray diffraction pattern in which the peak positions are substantially in accordance with the peak positions of the pattern shown in FIG. 2.

6. The crystalline free base form of claim 3, wherein the crystalline free base form is characterized by a powder x-ray diffraction pattern in which the peak positions are substantially in accordance with the peak positions of the pattern shown in FIG. 3.

7. The crystalline free base form of claim 1, wherein the crystalline free base form is characterized by a differential scanning calorimetry trace which shows a maximum endothermic heat flow in the range of about 132° C. to about 138° C.

8. The crystalline free base form of claim 2, wherein the crystalline free base form is characterized by a differential scanning calorimetry trace which shows a maximum endothermic heat flow in the range of about 142° C. to about 150° C.

9. The crystalline free base form of claim 3, wherein the crystalline free base form is characterized by a differential scanning calorimetry trace which shows a maximum endothermic heat flow in the range of about 134° C. to about 140° C.

10. The crystalline free base form of claim 1, wherein the crystalline free base form is characterized by a differential scanning calorimetry trace which is substantially in accordance with that shown in FIG. 4.

11. The crystalline free base form of claim 2, wherein the crystalline free base form is characterized by a differential scanning calorimetry trace which is substantially in accordance with that shown in FIG. 5.

12. The crystalline free base form of claim 3, wherein the crystalline free base form is characterized by a differential scanning calorimetry trace which is substantially in accordance with that shown in FIG. 6.

13. The crystalline free base form of any one of claims 1 and 4-12, wherein the crystalline free base form is micronized.

* * * * *

UNITED STATES PATENT AND TRADEMARK OFFICE
CERTIFICATE OF CORRECTION

| | | |
|---|---|---|
| PATENT NO. | : 7,880,010 B2 | Page 1 of 1 |
| APPLICATION NO. | : 11/789154 | |
| DATED | : February 1, 2011 | |
| INVENTOR(S) | : Jennifer Bolton et al. | |

It is certified that error appears in the above-identified patent and that said Letters Patent is hereby corrected as shown below:

In Column 44, at line 9, "claims 1" should read "claims 1-3".

Signed and Sealed this
Seventeenth Day of May, 2011

David J. Kappos
*Director of the United States Patent and Trademark Office*